US008628533B2

(12) United States Patent
Graham et al.

(10) Patent No.: US 8,628,533 B2
(45) Date of Patent: Jan. 14, 2014

(54) BONE PLATE WITH REDUCTION AIDS AND METHODS OF USE THEREOF

(75) Inventors: Thomas James Graham, Timonium, MD (US); Louise M. Focht, Del Mar, CA (US)

(73) Assignee: The Cleveland Clinic Foundation, Cleveland, OH (US)

( * ) Notice: Subject to any disclaimer, the term of this patent is extended or adjusted under 35 U.S.C. 154(b) by 895 days.

(21) Appl. No.: 12/117,666

(22) Filed: May 8, 2008

(65) Prior Publication Data

US 2009/0281577 A1 Nov. 12, 2009

(51) Int. Cl.
*A61B 17/56* (2006.01)
*A61B 17/58* (2006.01)
*A61B 17/80* (2006.01)
*A61F 2/30* (2006.01)

(52) U.S. Cl.
USPC ............... 606/70; 606/280; 606/71; 606/286

(58) Field of Classification Search
USPC ..................... 606/69–75, 279–299
See application file for complete search history.

(56) References Cited

U.S. PATENT DOCUMENTS

| 565,255 | A | 8/1896 | Belden |
| 583,455 | A | 6/1897 | Bush |
| 1,608,790 | A | 11/1926 | Henslow |
| 2,031,483 | A | 2/1936 | Interrante |
| 2,031,484 | A | 2/1936 | Interrante |
| 3,939,828 | A | 2/1976 | Mohr et al. |
| 4,120,298 | A * | 10/1978 | Fixel ............................... 606/70 |
| 4,409,970 | A | 10/1983 | Carrel |
| 4,658,822 | A | 4/1987 | Kees, Jr. |
| 4,726,808 | A * | 2/1988 | Collins ....................... 623/17.17 |
| 4,838,254 | A | 6/1989 | Gauthier |
| 4,852,559 | A | 8/1989 | Chernoff |
| 5,006,120 | A | 4/1991 | Carter |
| 5,013,314 | A | 5/1991 | Firica et al. |
| 5,092,889 | A | 3/1992 | Campbell, Jr. |
| 5,312,426 | A | 5/1994 | Segawa et al. |
| 5,372,604 | A | 12/1994 | Trott |
| 5,374,268 | A | 12/1994 | Sander |
| 5,441,509 | A | 8/1995 | Vidal et al. |
| 5,484,439 | A * | 1/1996 | Olson et al. ..................... 606/65 |
| 5,487,746 | A | 1/1996 | Yu et al. |
| 5,507,747 | A | 4/1996 | Yuan et al. |
| 5,522,902 | A * | 6/1996 | Yuan et al. .................. 623/22.41 |
| 5,586,985 | A | 12/1996 | Putnam et al. |
| 5,674,222 | A * | 10/1997 | Berger et al. ................... 606/71 |
| 5,709,682 | A | 1/1998 | Medoff |
| 5,718,704 | A | 2/1998 | Medoff |
| 5,931,839 | A | 8/1999 | Medoff |
| 5,935,128 | A | 8/1999 | Carter et al. |

(Continued)

*Primary Examiner* — Sameh Boles
*Assistant Examiner* — Samuel Hanna
(74) *Attorney, Agent, or Firm* — Tarolli, Sundheim, Covell & Tummino LLP

(57) ABSTRACT

Aspects of the present disclosure include a bone plate and/or a bone plate system. The bone plate includes an elongate body, which body includes a distal portion and a proximal portion. The proximal portion includes at least one projection extending there from, which projection is configured for contacting a bone portion, e.g., a fractured bone portion, so as to aid in the reduction thereof. In some variations, the proximal portion includes a plurality of projections, e.g., reduction aids. Methods of using such a bone plate having reduction aids by itself, or in conjunction with a second bone plate, for the reduction, restoration and treatment of a bone fracture are also provided.

14 Claims, 10 Drawing Sheets

(56) References Cited

U.S. PATENT DOCUMENTS

| | | | |
|---|---|---|---|
| 5,941,878 A * | 8/1999 | Medoff | 606/60 |
| 6,066,141 A | 5/2000 | Dall et al. | |
| 6,077,266 A | 6/2000 | Medoff | |
| 6,113,603 A | 9/2000 | Medoff | |
| 6,248,109 B1 | 6/2001 | Stoffella | |
| 6,302,884 B1 | 10/2001 | Wellisz et al. | |
| 6,302,887 B1 | 10/2001 | Spranza et al. | |
| 6,440,135 B2 | 8/2002 | Orbay et al. | |
| 6,464,710 B1 | 10/2002 | Foster | |
| 6,554,835 B1 | 4/2003 | Lee | |
| 6,652,530 B2 | 11/2003 | Ip et al. | |
| 7,037,308 B2 | 5/2006 | Medoff | |
| 7,090,676 B2 | 8/2006 | Huebner et al. | |
| 7,189,237 B2 | 3/2007 | Huebner | |
| 7,229,445 B2 | 6/2007 | Hayeck et al. | |
| 7,235,079 B2 | 6/2007 | Jensen et al. | |
| 7,250,053 B2 | 7/2007 | Orbay | |
| 7,316,687 B2 | 1/2008 | Aikins et al. | |
| 7,326,212 B2 | 2/2008 | Huebner | |
| 2002/0095157 A1 | 7/2002 | Bowman | |
| 2002/0143339 A1 | 10/2002 | Medoff | |
| 2002/0147452 A1 | 10/2002 | Medoff et al. | |
| 2004/0158251 A1 | 8/2004 | Morrison et al. | |
| 2004/0230312 A1 | 11/2004 | Hanson et al. | |
| 2005/0010226 A1 * | 1/2005 | Grady et al. | 606/69 |
| 2005/0010228 A1 * | 1/2005 | Medoff | 606/74 |
| 2005/0070902 A1 | 3/2005 | Medoff | |
| 2005/0154392 A1 | 7/2005 | Medoff et al. | |
| 2005/0234458 A1 | 10/2005 | Huebner | |
| 2005/0245931 A1 | 11/2005 | Orbay | |
| 2006/0015101 A1 | 1/2006 | Warburton et al. | |
| 2006/0089648 A1 | 4/2006 | Masini | |
| 2006/0155284 A1 | 7/2006 | Doherty et al. | |
| 2006/0173458 A1 | 8/2006 | Forstein et al. | |
| 2006/0189992 A1 * | 8/2006 | Medoff | 606/72 |
| 2006/0217722 A1 * | 9/2006 | Dutoit et al. | 606/69 |
| 2006/0229619 A1 * | 10/2006 | Orbay et al. | 606/69 |
| 2006/0241612 A1 | 10/2006 | Medoff | |
| 2007/0118126 A1 | 5/2007 | Medoff et al. | |
| 2007/0123880 A1 | 5/2007 | Medoff | |
| 2007/0173841 A1 * | 7/2007 | Ralph et al. | 606/69 |
| 2008/0077132 A1 * | 3/2008 | Medoff | 606/60 |
| 2009/0043310 A1 | 2/2009 | Rasmussen | |
| 2009/0069851 A1 * | 3/2009 | Gillard et al. | 606/280 |
| 2009/0118770 A1 * | 5/2009 | Sixto, Jr. et al. | 606/280 |

\* cited by examiner

BONE PLATE WITH REDUCTION AIDS AND METHODS OF USE THEREOF

BACKGROUND

A bone fracture is a condition of a bone in which at least a portion of the bone has cracked, broken, and or fragmented. Bone fractures can be caused in several different ways, for instance, as a result of a high force impact, stress, or as the result of conditions that presuppose the bones for fracturing, such as osteoporosis, cancer, and the like. Fractures may be closed or compound and they may be simple or multi-fragmentary, e.g., comminuted.

The ease and success of treatment of bone fractures often depends on the type and location of the fracture and the tools available for correcting the crack, break, and/or fragmentation of the bone to be treated. For instance, a closed, simple fracture along a diaphyseal portion of a long bone may be relatively simple to correct and therefore treat. However, a distal peri-articular bone fracture of the distal radius, due to its location and the morphology of the bones involved, may be difficult to correct and treat.

There are several methods for treating bone fractures, all of which typically involve the stabilization of the bone fragments. For instance, the fractured bone pieces may be reduced, e.g., aligned, and restored to their natural position, which position is then maintained using standard immobilization techniques, such as using plaster or fiberglass casts, as well as implanting surgical nails, screws, plates, and wires which function to fix and hold the fractured bone together.

However, the use of casts and typical surgical nails, screws, plates, and wires for the treatment of fractured bones have several drawbacks. For example, casts are problematic in that they are big, bulky and usually only allow a small degree of motion of associated joints. Further, casts often fail to provide adequate internal fixation, thus, resulting in pain, deformity, and/or prolonged disability. Additionally, the use of typical nails, screws, plates, and wires can be problematic because these devices may be hard to apply, are not easily manipulated so as to appropriately reduce and fix the bone in correct alignment, and are not suited for reducing fragments, e.g. multiple fracture portions, that are displaced from the main loci of the fracture, often requiring additionally plating and/or wiring.

The details of one or more variations of the subject matter described herein are set forth in the description below and the accompanying drawings. Other features and advantages of the subject matter described herein will be apparent from the description and drawings, and from the claims.

SUMMARY

Aspects of the present disclosure include a bone plate and/or a bone plate system. The bone plate includes an elongate body, which body includes a distal portion and a proximal portion. The distal portion includes at least one projection extending there from, which projection is configured for contacting a bone portion, e.g., a fractured bone portion, so as to aid in the reduction thereof. In some variations, the distal portion includes a plurality of projections, e.g., reduction aids. Further, in some variations, the distal portion may additionally be configured for engaging one or more of a bone portion and a second bone plate, such as juxtaarticular extension plate.

Accordingly, in certain aspects, the present disclosure is directed to a bone plate system, which system may include at least a first bone plate, such as a primary bone plate having one or more reduction aids extending there from, as described above, and a second bone plate. The first and second bone plates of the system may be affixed to one or more bone portions, and/or each other, so as to reduce, align, and stabilize one or more bone portions and thereby correct and/or treat a bone fracture. For instance, in certain variations, the bone plate system includes at least a first bone plate, e.g., a diaphyseal bone plate having one or more reduction aids extending there from, and a second bone plate, e.g., a peri-articular bone plate, which bone plates may be configured so as to be coupled together and/or to attach to one or more fragmented bone pieces and thereby be used to reduce and/or fix a fractured bone portion for the treatment thereof.

Methods of using such bone plates and bone plate systems for the reduction and/or the restoration and/or treatment of bone fractures, for example, are also provided herein.

BRIEF DESCRIPTION OF THE DRAWINGS

According to common practice, the various features of the drawings may not be presented to-scale. Rather, the dimensions of the various features may be arbitrarily expanded or reduced for clarity. Included in the drawings are the following figures:

FIGS. 1D-1E depicts a secondary bone plate of the disclosure; as depicted both bone plates include projections extending there from. FIG. 1A provides a top, front view of the primary bone plate. FIG. 1B provides a top, perspective view of the primary bone plate. FIG. 1C provides a side view of the primary bone plate. FIG. 1D provides a top, perspective view of a secondary bone plate. FIG. 1E provides a side view of the secondary bone plate of FIG. 1D.

Like reference symbols in the various drawings indicate like elements.

DEFINITIONS

Figure 1A:
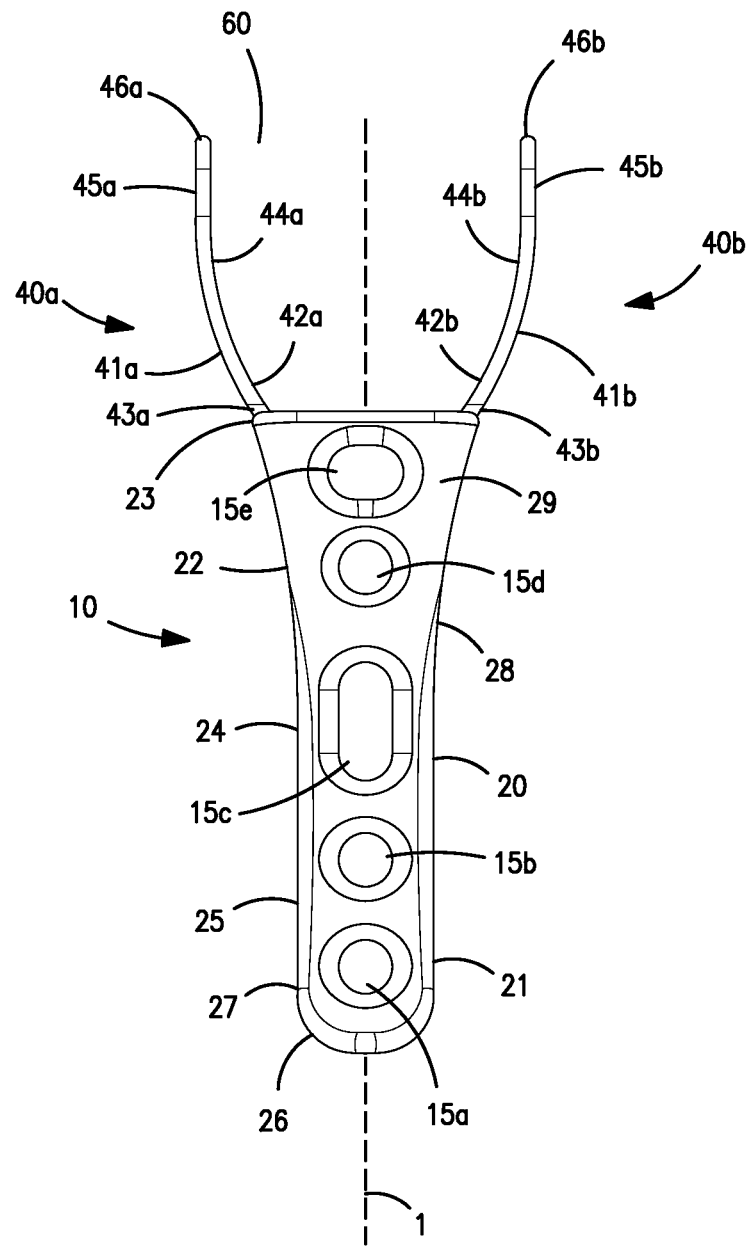
FIGS. 1A-C depicts a primary bone plate of the disclosure.

Before the present subject matter is further described, it is to be understood that this subject matter described herein is not limited to particular embodiments described, as such may of course vary. It is also to be understood that the terminology used here in is for the purpose of describing particular embodiments only, and is not intended to be limiting. Unless defined otherwise, all technical terms used herein have the same meaning as commonly understood by one skilled in the art to which this subject matter belongs.

Where a range of values is provided, it is understood that each intervening value, to the tenth of the unit of the lower limit, unless the context clearly dictates otherwise, between the upper and lower limit of that range, and any other stated or intervening value in that stated range, is encompassed within the subject matter described herein. The upper and lower limits of these smaller ranges may independently be included in the smaller ranges, and are also encompassed within the subject matter described herein, subject to any specifically excluded limit in the stated range. Where the stated range includes one or both of the limits, ranges excluding either or both of those included limits are also included in the subject matter described herein.

It must be noted that as used herein and in the appended claims, the singular forms "a", "and", and "the" include plural referents unless the context clearly dictates otherwise. Thus, for example, reference to a "fastener" includes a plurality of such fasteners, and reference to "the opening" includes reference to one or more openings and equivalents thereof known to those skilled in the art, and so forth.

It is further noted that the claims may be drafted to exclude any optional element. As such, this statement is intended to serve as antecedent basis for use of such exclusive terminology as "solely", "only" and the like, in connection with the recitation of claim elements, or the use of a "negative" limitation. Accordingly, the term "optional" or "optionally present," as in an "optional element," or an "optionally present element," means that the subsequently described element may or may not be present, so that the description includes instances where the element is present and instances where it is not.

As will be apparent to those of skill in the art upon reading this disclosure, each of the individual embodiments described and illustrated herein has discrete components and features which may be readily separated from or combined with the features of any of the other several embodiments without departing from the scope of the subject matter described herein. Any recited method can be carried out in the order of events recited or in any other order which is logically possible.

DETAILED DESCRIPTION

An aspect of the present disclosure includes a bone plate. The bone plate may have any suitable shape and have any suitable size, so long as the primary bone plate includes an extended body that is capable of being attached to a bone portion, and further includes at least one projection, e.g., a plurality of projections, extending from the extended body that is configured to assist in the reduction and/or stabilization of a fracture of the bone portion so as to treat the bone fracture. In certain embodiments, the bone plate as defined herein may be a primary or a secondary bone plate. For instance, the bone plate may be a primary bone plate, which bone plate may be an elongate plate member that includes a distal portion with a distal end, one of which distal portion or distal end includes a plurality of projections extending therefrom, a proximal portion with a proximal end, and an intercalating portion between the proximal and distal portions.

Specifically, the first and second ends of the bone plate are separated from one another by a separation that defines a length of the subject bone plate. In certain embodiments, and dependent on the context, the proximal portion of the bone plate refers to a region of the bone plate that is closest to the core of the subject upon which the bone plate is to be positioned. For instance, where the bone plate is intended to be attached lengthwise to a diaphyseal bone portion the proximal end is that end of the bone plate that points toward the core of the subject. Likewise, the distal portion of the bone plate refers to a region of the bone plate that is further away from the core of the subject upon which the bone plate is to be positioned. For instance, where the bone plate is intended to be attached lengthwise to a diaphyseal bone portion the distal end is that end of the bone plate that points away from the core of the subject.

The primary bone plate additionally includes a top and a bottom surface as well as a first and a second side. The top and bottom surface are separated from one another by a distance, which distance defines a thickness. The first and second sides are also separated from one another, which separation defines a width. The bottom surface may be configured for contacting a bone surface, and may be referenced herein as a bone contacting surface. The top surface is opposite the bone contacting surface.

The primary bone plate may have a length that ranges from about 5 mm or less to about 50 mm or more, such as about 10 mm to about 40 mm, for instance, between about 15 mm to about 30 mm, such as between about 20 mm to about 25 mm. The primary bone plate may have a thickness that ranges from about 0.01 mm to about 5 mm, for instance, between about 0.1 mm to about 3 mm, such as between about 0.5 mm or about 1 mm to about 2 mm or about 2.5 mm. The primary bone plate of the subject disclosure may have a width that ranges from about 3 mm to about 50 mm, for instance, between about 5 mm to about 50 mm, such as between about 8 mm or about 10 mm to about 20 mm or about 35 mm, for instance, about 25 mm to about 30 mm.

The length of the primary bone plate may be fixed or it may be variable. For instance, the primary bone plate may include an intercalating portion wherein length of the intercalating portion may be variable. For instance, the intercalating portion may be fabricated from a material and in such a manner that it resists deformation, or it may be fabricated from a material and in such a manner that it is capable of being bent or shaped before use. Accordingly, the length and/or shape of the intercalating portion may be adjustable.

In certain embodiments, the primary bone plate includes a portion that contains at least one projection or tine. For instance, a proximal or a distal portion of the primary bone plate may include a plurality of projections, such as a plurality of projections that extend away from the bone plate. In certain embodiments, the projections extend away from a proximal or distal end of the primary bone plate. The projections may be contiguous with the elongated body of the primary bone plate. For example, the projections may be fabricated along with and from the same material of which the elongated body is made such that the elongated body and the one or more projections form a singular whole.

The projections or tines may have any suitable configuration so long as at least a portion of the projections is configured for contacting or otherwise engaging a bone portion, such as a fractured and/or fragmented bone portion that is located distally from a primary bone portion. For instance, where the elongated body of the primary bone plate is configured for contacting and/or engaging a primary bone portion, such as a diaphyseal bone portion of a long bone, the projections may be adapted for contacting and/or engaging a bone portion, such as a fractured and distally located diaphyseal, peri-articular, juxta-articular, and/or metaphyseal bone portion, e.g., in the upper or lower extremities.

For example, in certain embodiments, the projections not only contact a fractured bone portion located distally from the elongate body of the primary bone plate, but are also adapted for assisting in the aligning of the fractured distal bone portion with a primary bone portion, such as a primary bone portion contacted and/or engaged by the elongated body of the primary bone plate.

Thus, a projection as used herein may also be referred to as reduction aid, in that it may aid in reducing a fractured and/or fragmented bone portion in correct anatomical alignment, for instance, with respect to a non-fractured bone portion. In this manner a projection, or reduction aid, of the primary bone plate may function, in part, to stabilize, align and reduce a fractured bone portion, such as a commutated distal juxtaarticular fracture of the radius bone or ulna bone. It is to be noted that reference to "a bone" and/or "a bone portion" as used herein is not limited to a single bone and/or a single bone portion, but rather one or more bones or one or more bone portions pertaining to one or more separate bones may be referred to thereby.

A projection or reduction aid of the subject disclosure includes a proximal or bone plate contacting portion and a distal or bone contacting portion. The projection may also include an intercalating portion positioned between the proximal and distal portions of the projection. One or more of the portions of the projection may be tubular or non-tubular, flattened, rounded, elliptical, square, rectangular, hexagonal, or the like. For instance, the body or intercalating portion of the projections may be configured as an extended tine or prong that is rounded, square or rectangular in cross section. In certain embodiments, the body of the projection may be extended and may include one or more surfaces, such as a top, bottom, or side surface, that is flattened in shape. The body of the projection may be curved or substantially straight.

Additionally, the distal or bone contacting portion of the projection may be of any suitable shape and of any suitable size, so long as the bone contacting portion is capable of contacting and/or otherwise engaging a bone portion, such as a fractured or fragmented bone portion that is located distally from the elongate body of the primary bone plate. For instance, the bone contacting portion of the projection may be flattened, rounded, elliptical, square, rectangular, it may be curved, concave, convex, substantially straight, angled, or otherwise configured to conform to the bone portion to which it is configured to be contacted, engaged, or otherwise associated. The bone contacting portion may include one or more openings, such as an opening configured for receiving a fastener there through.

The projection may be positioned along a side or an end of the primary bone plate. For instance, in certain embodiments, a plurality of projections are included, for example, two projections, wherein the projections are positioned at a distal or proximal end of the primary bone plate and extend longitudinally away from the bone plate, so as to form a forked or fork like configuration. In certain embodiments, a plurality of projections are included wherein at least one of the plurality of projections is positioned on opposite sides of the primary bone plate, so as to form a y or y-like configuration.

The one or more projections may extend axially away from a side of the primary bone plate such that an angle is formed between the projection and the side of the primary bone plate. The angle may be any suitable angle and may range from about 1° to about 90° with respect to a proximal or distal end of the primary bone plate, such as about 5° to about 45° for instance, about 10° to about 30°, including about 15° to about 20°. Accordingly, where two or more projections are included, one or more than one projection may be angled with respect to a primary plan defined by the longitudinal axis of the bone plate. For instance, where two projections are included, one projection may be angled and the other projection may not be angled. Alternatively, both projections may be angled. The angle may be with respect to a bottom or top surface of the bone plate or with respect to a side thereof. Hence, the projection may be angled the dorsal, volar, radial, or ulnar directions. The projections could be angled so as to be convergent or divergent.

Additionally, where a top or bottom surface of the elongated body of the primary plate defines a primary plane, the one or more projections may extend away from the elongate body at an angle with respect to the primary plane. Such an angle may range from about 0° to about 90° with respect to a primary plane defined by the top or bottom surface, extending between the proximal and distal ends of the primary bone plate, such as about 5° to about 45° for instance, about 10° to about 30°, including about 15° to about 20°. In certain embodiments, the body of the projection of the primary bone plate may include an internal arced or curved portion, wherein the curve includes a degree of curvature that ranges from about 1 mm to about 50 mm, for instance, about 5 mm to about 30 mm, including about 10 mm to about 20 mm, including about 15 mm.

Accordingly, the primary bone plate may include one or more projections, for instance, two projections, positioned along opposing sides of the primary bone plate so as to form a Y or fork shaped configuration, wherein the area between the two extended projections is configured for receiving or being received within a bone portion. For instance, the projections of the primary bone plate may be configured for contacting an outside or inside surface of a bone portion. Hence, the bone contacting and/or intercalating portion of the projections may be referred to as extramedullary or intramedullary bone contacting or intercalating portions.

In certain embodiments, the one or more projections may be inwardly or outwardly biased. For instance, a projection may be biased such that when positioned in relation to a bone portion it presses against an outer or inner surface of the bone portion. For example, where two or more projections are included, one or both of the projections may be configured such that when the projection contacts an outer surface of a bone portion it presses inwards, and/or one or both of the projections may be configured such that when it contacts an inner surface of a bone portion it presses outwards.

Thus, in certain embodiments, a plurality of projections extend away from the primary bone plate and contact an outer surface of a bone portion, e.g., a fractured and/or displaced bone portion, and the projections help reduce the fractured and/or displaced bone portion, in some instances, by pressing against the outer surface (e.g., inwards) of the bone portion. Also, in certain embodiments, a plurality of projections extend away from the primary bone plate, are inserted through an opening of the bone, and contact or are otherwise associated with an inner surface of a bone portion, e.g., a fractured and/or displaced bone portion, and help reduce the fractured and/or displaced bone portion, in some instances, by pressing outwards against the inner surface of the bone portion. In certain variations, the plurality of projections extend from a distal end or a distal portion of the bone plate. In certain variations, the plurality of projections extend from a proximal end or a proximal portion of the bone plate.

Accordingly, the one or more projections of the primary bone plate may be extramedullary in that the projections contact, engage, and/or are otherwise associated with an outer bone surface of a fractured bone portion. In certain embodiments, the one or more projections may be intramedullary, in that they are configured so as to be inserted through an opening, for instance, an opening in a fractured bone portion, and are adapted to be contacted, engaged, or otherwise associated with an internal bone surface of a fractured bone portion. In certain variations, at least one projection is configured for being extramedullary and at least one projection is configured for being intramedullary.

The primary or secondary bone plate including the projections thereof may be fabricated from any suitable material and in any suitable manner. Specifically, a subject bone plate of the disclosure may be fabricated from any suitable biocompatible material so long as the bone plate(s) is of sturdy yet malleable construction. For instance, in certain embodiments, the bone plate may be fabricated from a suitable metal material containing a metal such as stainless steel, titanium, cobalt chromium, and/or an alloy thereof. Further, suitable materials may be a bioabsorbable material such as polygalactic acid (PGA), polylactic acid (PLA), copolymers thereof, and the like. Other suitable materials include plastic, ceramics, and the like. In general, the bone plate may be fabricated from a suitable material so as to resist deformation and to be stiffer and stronger than the section of bone spanned by the extender plate, yet flexible enough not to significantly strain the bone. In certain embodiments, a bone plate with projections may be fabricated in accordance with methods including stamping, machining, casting, laser cutting, molding, and the like.

In certain embodiments, the bone plate or a portion thereof may be fabricated from a material that may be bent or formed intraoperatively to accommodate the shape of the bone. For instance, the type and strength characteristics of the material used to form the bone plate, or a portion thereof, may be selected such that the material and the portion it comprises is such that it may be deformed as desired and yet keep the shape of the deformation.

Dependent on the dimensions and shape of its configuration and the use to which it is to be put, the primary bone plate may be adapted so as to be associated with any suitable bone portion. For instance, in some embodiments, the primary bone plate is configured for being associated with, e.g., attached to, a shaft portion of a long bone. For instance, in certain embodiments, the primary bone plate is configured for being attached to a diaphyseal portion of a bone, and therefore, the primary bone plate may be referenced herein as a diaphyseal bone plate.

Accordingly, the primary bone plate, e.g., a diaphyseal bone plate, may be configured so as to be complimentary to a bone morphology, such as the long bone morphology of a diaphyseal bone. In certain embodiments, the primary bone plate has a configuration that is complimentary to a planar portion of a bone portion and in certain embodiments, the primary bone plate has a configuration that is complimentary to a non-planar portion of a bone portion.

Hence, the primary bone plate may be substantially planar, for instance, where the proximal and distal ends of the bone plate define a primary plane. For instance, in certain embodiments, at least one of the primary bone plate bone contacting surface and the primary bone plate top surface substantially corresponds to a primary plane, wherein the primary plane is substantially linear. However, in certain embodiments, at least one of the primary bone plate bone contacting surface and the primary bone plate top surface corresponds to a primary plane, wherein the primary plane is non-linear, or arced.

For example, the primary bone plate may be non-planar and may have a configuration that is adapted to conform to a specific non-planar bone morphology, such as a configuration that is adapted to specifically and snugly fit the bone morphology to which the bone plate is to be associated and/or attached. Hence, in certain embodiments, the primary bone plate includes an internal angled and/or arced portion between the proximal and distal ends thereof and is therefore angled and/or arced in correspondence to a bone surface to which the plate is to be associated.

For instance, in certain embodiments, the bone contacting surface between the proximal and distal ends of the primary bone plate may include an internal angled portion, wherein the angle may range from about 1° to about 90°, such as from about 5° to about 45°, for instance from about 7.5° to about 30°, including from about 10° to about 20°, such about as 15°. The bone contacting surface between the proximal and distal ends of the primary bone plate may include an internal arced portion, wherein the arc includes a radius of curvature that ranges from about 1 mm to about 50 mm, for instance, from about 5 mm to about 30 mm, including from about 10 mm to about 20 mm, such about as 15 mm.

Further, in certain embodiments, the primary bone plate includes a curved portion between the first and second sides thereof and is therefore curved relative to a central, longitudinal axis defined by the proximal and distal ends of the primary bone plate. For instance, in certain embodiments, the primary bone plate may include an internal concave portion between the first and second sides of the bone plate. The concaved portion may run along a partial or entire length of the primary bone plate, wherein the curvature comprises a degree of curvature, e.g., a concavity that ranges from about 5 mm to about 20 mm, such as about 7 mm to about 18 mm, including about 10 mm to about 15 mm.

In certain embodiments, the bone plate includes concave portion. For example, in certain embodiments, the proximal portion of the primary bone plate, e.g., the portion adapted to be associated with a first bone portion, may include a concave configuration adapted to fit around a convex bone portion, while the proximal portion is substantially planar. In certain embodiments, the proximal portion of the primary bone plate may include a concave configuration while the distal portion is substantially planar.

In certain embodiments, the proximal portion of the primary bone plate may be planar, and a top or bottom surface of the primary bone plate may include a groove or slot portion that is configured for receiving an insertion member, e.g., a tab insertion portion, of a secondary bone plate. Accordingly, although in some embodiments, the primary bone plate is configured for engaging and/or being affixed or otherwise associated with a bone portion without being associated with or coupled to a secondary bone plate; in other embodiments, the primary bone plate is configured for being affixed or otherwise associated with a bone portion and is adapted for engaging or being associated with an additional, e.g., secondary bone plate.

For instance, the proximal portion of the primary bone plate may be configured for engaging or otherwise being associated with a portion of bone, e.g., a first bone portion, and the distal portion may be configured for being associated with an additional bone plate and/or another portion of bone, e.g., a second bone portion. Specifically, in certain embodiments, the distal portion of the primary bone plate may include a bone plate engagement element, such as a peri-articular bone plate engagement element, e.g., where the secondary bone plate is a peri-articular bone plate.

Where included, a bone plate engagement element of the primary bone plate may have any suitable configuration so long as it is capable of facilitating an association and/or coupling of the primary bone plate with an additional bone plate. For instance, the engagement element of the primary bone plate may be a configuration that is adapted to allow the primary bone plate to be associated with a secondary bone plate. Hence, the engagement element may include a recess, groove or slot-like configuration positioned at a proximal portion of the primary bone plate, which is adapted to receive a corresponding engagement portion, e.g., a tab portion, of a secondary bone plate and thereby be mated therewith.

For example, where a secondary bone plate includes an engagement element (e.g., a primary bone plate engagement element) configured as an extended male insertion portion (e.g., a tab insertion portion), the primary bone plate may include a recessed engagement portion (e.g., a secondary bone plate engagement element) that is configured as a cut-out female tab receiving portion that is adapted to receive the insertion portion of the secondary bone plate. The engagement element of the primary bone plate may also be configured as a grooved portion within which is fitted the tab insertion portion of the secondary bone plate. Accordingly, the primary bone plate engagement element may include one or both of a recessed portion and a groove-like configuration in to which the insertion portion slides. In certain embodiments, the engagement element is hooded, e.g., the distal end of the primary bone plated includes an orifice into which the tab portion of an additional plate is inserted.

Accordingly, in certain embodiments, the engagement element of the primary bone plate is configured as a receptacle or tab receiving portion, wherein the receptacle portion has a first width that ranges from about 2 mm to about 20 mm, for instance, between about 5 mm to about 15 mm, such as between about 7 mm and about 10 mm. In certain embodiments, the receptacle portion has a second width that ranges from about 1 mm to about 18 mm, for instance, between about 3 mm to about 14 mm, such as between about 5 mm and about 7 mm or about 8 mm or about 10 mm. In certain embodiments, the first and second widths are distanced from one another such that the receptacle or tab receiving portion tapers along its length. In certain embodiments, the engagement element may have a length that ranges from about 5 mm to about 30 mm, for instance, between about 7.5 mm to about 25 mm, such as between about 10 mm to about 15 mm or about 20 mm. In certain embodiments, the engagement member may have a thickness that ranges from about 0.1 mm to about 3 mm, for instance, between about 0.25 mm to about 2 mm, such as between about 0.5 mm or 1 mm to about 1.5 mm. In certain embodiments, the engagement element positioned at the proximal portion of the primary bone plate, and may be centered between a plurality of projections, which give the primary bone plate a forked or y configuration.

The distal portion of the primary bone plate may itself be angled with respect to a proximal portion and/or a proximal end of the primary bone plate. For instance, a plane defined by a top surface of the distal portion of a primary bone plate elongated body may be angled with respect to the a plane defined by a top surface of the proximal portion of the primary bone plate elongated body such that an engagement element positioned at the distal portion of the primary bone plate is angled with respect to the proximal portion of the primary bone plate. In certain embodiments, the angle between the planes defined by the two surfaces may range from about 10 to about 900, such as from about 5° to about 45°, for instance from about 7.5° to about 30°, including from about 10° to about 20°, such about as 15°. In certain embodiments, the engagement element positioned at the distal portion of the primary bone plate is not angled but rather is planar with respect to the distal end of the primary bone plate.

Accordingly, another aspect of the present disclosure includes a bone plate system. The bone plate system may include at least a first bone plate, as described above, and a second bone plate, which bone plates may be affixed to one or more bone portions and/or each other, so as to align and stabilize the bone and thereby correct and/or treat a bone fracture. In certain variations, at least one of the primary and secondary bone plates include one or more reduction aids projecting there from. The projections may project from a proximal or distal surface or from the sides of the bone plate and may be configured as described above. For instance, in certain variations a plurality of projections are included wherein the projections are adjacent to and/or straddle a bone plate engagement element.

Accordingly, in certain variations, the bone plate system disclosed herein may include at least a primary bone plate, having one or a plurality of projections or reduction aids extending there form, and a second bone plate, which bone plates may be configured so as to be coupled together and/or to attach to one or more fragmented bone portions and thereby be used to reduce and/or fix a fractured bone portion for the treatment thereof.

Hence, in certain embodiments, the present disclosure is directed to a bone plate system that includes a second bone plate (sometimes referred to herein as a secondary bone plate). A secondary bone plate of the subject plate system may have any suitable shape and have any suitable size so long as the secondary bone plate is capable of being coupled to a primary bone plate and/or associated with a bone portion, e.g., a second and/or third bone portion, so as to assist in the reduction and/or stabilization of one or more bone portions and thereby treat a bone fracture. The secondary bone plate may be an elongate plate member that includes a proximal portion with a proximal end, a distal portion with a distal end, and an intercalating portion between the proximal and distal portions.

Specifically, the first and second ends are separated from one another, which separation defines a length of the subject plate. In certain embodiments, and dependent on the context, a proximal portion of the secondary bone plate refers to a region of the secondary bone plate that is closest to the core of the subject's body to which the secondary bone plate is intended to be applied. Typically, the proximal portion of the secondary bone plate includes a portion that is configured for being coupled to a primary bone plate, such as a primary bone plate with reductions aids, and/or associated with or other wise attached to a portion of bone, e.g., a second bone portion, whereas a distal portion of a secondary bone plate of the subject bone plate system, refers to a region of the bone plate that is further away from the subject's core and contains a portion that is configured for being contacted and/or attached to another bone portion, e.g., a third bone portion.

Additionally, the secondary bone plate includes a top and a bottom surface, wherein the top and bottom surface are separated from one another, the separation of which defines a thickness. In certain embodiments, the secondary bone plate includes a bottom surface that is configured for contacting a bone surface and therefore may be referenced as a bone contacting surface. Likewise, in certain embodiments, the secondary bone plate includes a top surface that is opposite the bone contacting surface. Further, the secondary bone plate includes at least a first side and a second side which sides are separated from each other by a distance, which distance defines a width.

In certain embodiments, the secondary bone plate may have a length that ranges from about 4 mm or less to about 50 mm or more, such as about 5 mm to about 40 mm, for instance, between about 8 mm to about 30 mm, such as between about 10 mm to about 25 mm, including about 15 mm to about 20 mm. In certain embodiments, the secondary bone plate may have a thickness that may range from about 0.01 mm or less to about 3 mm or more, for instance, between about 0.1 mm to about 2.5 mm, such as between about 0.5 mm or about 1 mm to about 1.5 or about 2 mm. In certain embodiments, a suitable secondary bone plate of the subject disclosure may have a width that ranges from about 3 mm or less to about 50 mm or more, for instance, between about 4 mm to about 30 mm, such as between about 5 mm or about 8 mm to about 25 mm or about 20 mm, for instance, about 10 mm to about 15 mm.

The secondary bone plate may also include an intercalating portion, e.g., a portion between the proximal and distal portions. The length of the intercalating portion may be fixed or variable. For instance, the intercalating portion may be fabricated from a material and in such a manner that it resists deformation, or it may be fabricated from a material and in such a manner that it is capable of being bent or shaped before use. Accordingly, the length and/or shape of the intercalating portion may be adjustable.

The secondary bone plate may include a proximal portion, wherein the proximal portion includes a primary bone plate engagement element. A primary bone plate engagement element of the secondary bone plate may have any suitable configuration so long as it is capable of facilitating an association and/or coupling of the secondary bone plate with a primary bone plate. For instance, the engagement element of the secondary bone plate may include a configuration that is adapted to allow the secondary bone plate to be associated with a first bone plate, e.g., a primary bone plate.

Hence, the secondary bone plate engagement element may include an extended portion, such as a tab insertion portion, that is configured for being inserted or otherwise associated with a groove, hooded, and/or slot-like configuration of a primary bone plate, wherein the engagement portion is positioned at a proximal portion of the secondary bone plate and is adapted to be coupled to a corresponding engagement portion, such as a tab receiving portion, of a primary bone plate and thereby be mated therewith. For example, where a primary bone plate includes an engagement element (e.g., a primary bone plate engagement element) configured as a female receiving portion (e.g., an insertion tab receiving portion), the secondary bone plate may include an extended engagement portion (e.g., a secondary bone plate engagement element) that is configured as an insertion member or tab that is adapted to be received within the receiving portion of the primary bone plate.

Accordingly, in certain variations, the engagement element of the secondary bone plate is configured as a tab insertion portion, wherein the tab insertion portion has a first width that ranges from about 1 mm or slightly less than 2 mm to about 18 mm or slightly less than 20 mm, for instance, between about 3 mm or slightly less than 5 mm, to about 14 mm or slightly less than 15 mm, such as between about slightly less than 7 mm to about slightly less than 10 mm. In certain variations, the tab insertion portion has a second width that ranges from about 1 mm to about slightly less than 18 mm, for instance, between about 3 mm or slightly less than 4 mm to about slightly less than 14 mm, such as between about 5 mm and about slightly less than about 7 mm or about 8 mm or about slightly less than 10 mm. In certain embodiments, the first and second widths are distanced from one another such that the tab insertion portion tapers along its length. In certain variations, the tab insertion portion may have a length that ranges from about 3 mm to about slightly less than 30 mm, for instance, between about 5 mm or slightly less than 6 mm to about slightly less than 25 mm, such as between about slightly less than 10 mm to about slightly less than 15 mm or about 20 mm. In certain variations, the engagement element may have a thickness that ranges from about 0.1 mm to about 3 mm, for instance, between about 0.25 mm to about 2 mm, such as between about 0.5 mm or 1 mm to about 1.5 mm.

It is to be noted that with respect to the above descriptions, the primary bone plate is described as including a female receiving engagement element, and the secondary bone plate is described as including a male insertion engagement element. Nevertheless, in certain embodiments, the primary bone plate includes a male insertion or tab-like engagement element, as that element is described above with respect to the secondary bone plate, and the secondary bone plate includes a female or tab receiving engagement element, as that element is described above with respect to the primary bone plate.

In certain variations, the engagement element positioned at the proximal portion of the secondary bone plate, and in some cases the proximal portion itself, is angled with respect to a distal portion and/or distal end of the secondary bone plate. For instance, a plane defined by a top surface of the proximal portion of the secondary bone plate body may be angled with respect to a plane defined by a top surface of the distal portion of the secondary bone plate body such that an engagement element positioned at the proximal portion of the secondary bone plate is angled with respect to the distal portion of the secondary bone plate.

Accordingly, in certain variations, the proximal portion containing the engagement element of the secondary bone plate may be angled with respect to the distal portion. For instance, in certain variations, there is an angle between the engagement element portion of the proximal portion of the secondary bone plate and the rest of the plate. In certain variations, the angle between the engagement element of the secondary bone plate and the rest of the plate may range from about 10 to about 90°, such as from about 5° to about 45°, for instance from about 7.5° to about 30°, including from about 10° to about 20°, such about as 15°. However, in certain variations, the engagement element positioned at the proximal portion of the secondary bone plate is not angled but rather is planar with respect to the distal end of the secondary bone plate.

In some variations, the secondary bone plate is configured for being associated with, e.g., contacted with and/or attached to a bone portion, such as an articulated portion of a bone, for instance, as a metaphyseal or epiphyseal bone portion. For example, in certain embodiments, the secondary bone plate may be configured for being attached to a peri-articular or juxta-articular portion of a bone, and therefore, the secondary bone plate may be referenced as a peri-articular or juxta-articlar bone plate. Hence, the secondary bone plate, may be configured so as to be complimentary to a bone morphology, such as the articulated bone morphology of a metaphysis or epiphysis bone portion. Accordingly, the secondary bone plate may have a configuration that is complimentary to a non-planar portion of an articulated bone portion.

For instance, the secondary bone plate may have a configuration that is adapted to conform to a specific bone morphology, such as a configuration that is adapted to specifically and snugly fit the bone morphology to which the secondary bone plate is to be contacted, associated, and/or attached. Thus, in certain embodiments, the secondary bone plate is non-planar. Consequently, there may be an angle between the proximal and distal portions of the secondary bone plate.

For example, in certain variations, a bone contacting surface of a proximal portion of a secondary bone plate may constitute a first or proximal plane of the secondary bone plate, and a bone contacting surface of a distal portion of a secondary bone plate may constitute a second or distal plane of the secondary bone plate, wherein the proximal and distal planes of the secondary bone plate are transverse to one another. Hence, the bone contacting surface between the proximal and distal portions and/or ends thereof of the secondary bone plate may include an internal angled portion. Accordingly, the angle between the planes defined by the proximal and distal bone contacting surfaces of the secondary bone plate may range from about 1° to about 90°, such as from about 5° to about 45°, for instance from about 7.5° to about 30°, including from about 10° to about 20°, such about as 15°. Additionally, although there may be an angle between the proximal and distal portions of the secondary bone plate, in certain variations, the proximal portion of the secondary bone plate is not angled with respect to a primary plane as defined by the primary bone plate. For instance, in certain variations, the proximal portion of the secondary bone plate is substantially coplanar with a primary plane of the primary bone plate.

Thus, in certain variations, the secondary bone plate includes an internal angled, curved, and/or arced portion between the proximal and distal ends thereof and is therefore angled, curved and/or arced in correspondence to a bone surface to which the plate is to be associated so as to model the morphology of the bone surface. Hence, the bone contacting surface between the proximal and distal ends of the secondary bone plate may include an internal curved portion, wherein the curve includes a degree of curvature that ranges from about 10 mm to about 50 mm, for instance, between about 15 mm to about 35 mm, such as between about 18 mm or about 20 mm to about 25 or about 30 mm.

Further still, in certain exemplary variations, the bone contacting surface between the proximal and distal ends of the secondary bone plate may include an internal arced portion, wherein the arc includes a radius of curvature that may be constant, increasing, or decreasing, depending in part on the length of the intercalating portion of the secondary bone plate. Accordingly, in certain variations, a bone contacting surface of the secondary bone plate includes an arc that has a decreasing radius of curvature that ranges from about 10 mm to about 50 mm, for instance, between about 15 mm to about 35 mm, such as between about 18 mm or about 20 mm to about 25 or about 30 mm. In certain embodiments, the secondary bone plate includes a curved and/or twisted portion whereby the twisted portion allows the secondary bone plate to extend outward and away from a primary bone plate so as to contact a bone surface that is positioned distally and out of plane with a bone contacting surface and/or a primary plane of the primary bone plate.

In certain variations, the secondary bone plate includes a curved or concave portion between the first and second sides thereof and is therefore curved relative to a central, longitudinal axis defined by the proximal and distal ends of the secondary bone plate. For instance, in certain variations, the secondary bone plate may include an internal concave portion between the first and second sides of the bone plate. The concaved portion may run along a partial or entire length of the secondary bone plate, wherein the curvature comprises a degree of curvature, e.g., a concavity, that ranges from about 5 mm to about 30 mm, for instance, between about 8 mm to about 30 mm, such as between about 10 mm or about 12 mm to about 20 mm or about 25 mm. In certain embodiments, the distal portion includes a concaved portion, while the proximal portion does not, e.g., a portion between the first and second sides of the secondary bone plate along the distal portion of the secondary bone plate are substantially flat or planar, and in certain embodiments, the proximal portion includes a concaved portion, while the proximal portion does not.

In certain variations, the secondary bone plate of the bone plate system includes a distal portion that is angled, curved, or arced, as described above, relative to a proximal portion, wherein the proximal portion of the secondary bone plate is relatively planar in relation to a primary plane defined by a top or bone contacting surface of the primary bone plate. In other variations, the proximal portion is angled, curved, or arced with respect to a primary plane defined by a top or bone contacting surface of the primary bone plate, but is in plane internally with respect to the distal portion of the secondary bone plate, that is the distal and proximal ends of the secondary bone plate may be in plane with one another (e.g., thus forming a secondary plane there between), which plane may transect or otherwise be out of plane from the primary plane of the primary bone plate. Accordingly, a portion or the entire secondary bone plate may be angled or curved with relationship to the primary bone plate.

In view of the above, the secondary bone plate may be angled in relationship to the primary bone plate in numerous ways such that the secondary bone plate, e.g., a peri-articular bone plate, includes a bone contacting surface that corresponds to one or more planes or an arc that are provided at an angle or substantially perpendicular to a primary plane defined by a primary bone plate. Accordingly, in certain variations, the secondary bone plate is angled with respect to a primary plane defined by the primary bone plate, wherein the angle may range from about 10 to about 90°, such as from about 50 to about 45°, for instance from about 7.5° to about 30°, including from about 10° to about 20°, such about as 150.

In certain variations, a bone plate of the disclosure includes a plurality of sections. For instance, in certain variations, the bone plate may include a first section, wherein the first section includes a bone plate engagement element, and a second section, wherein the second section includes a configuration adapted for contacting a bone surface. In certain variations, the second section is transverse to the second section.

For example, in certain variations, the bone plate may be configured so as to have a substantially "T" shape. Specifically, the first section may include a proximal portion with a proximal end, a distal portion with a distal end, and an intercalating portion; and the second section may be transverse to the first section and may include a proximal portion with a proximal end, a distal portion with a distal end, and an intercalating portion, wherein the intercalating portion, or another portion, of the second or transverse section is bisected by the distal portion of the first section, such that the secondary bone plate forms a "T" shape.

In certain variations, the first section of the bone plate is angled in relation to the second section. For instance, a top or bottom surface of the proximal portion of the first section may define a first plane, and a top or bottom surface of the distal portion of the first section and/or a top or bottom surface of the second section may define a second plane, wherein the first and second planes transect one another, such that the second section is out of plane of the first section.

Accordingly, in certain variations, a portion or the entire first section of the bone plate may be angled with respect to a portion or the entire second section of the secondary bone plate, wherein the angle may range from about 10 to about 90°, such as from about 5° to about 45°, for instance, from about 7.5° to about 30°, including from about 10° to about 20°, such about as 15°. In this manner, the secondary bone plate may have a "T" shaped configuration and may be configured so as to be associated with another bone plate, and further may be configured so as to contact a bone surface wherein the bone surface has an angled or curved morphology with respect to the plane of the primary bone plate.

The proximal and/or distal portions of the second section of the bone plate may be curved or angled with respect to the intercalating portion and/or each other. For instance, the second section may include a curvature, which curvature may span a portion or the entire length of the second section. In certain embodiments, one or more of the portions of the second section of the secondary bone plate are angled with respect to each other, wherein the angle may range from about 1° to about 90°, such as from about 5° to about 45°, for instance, from about 7.5° to about 30°, including from about 10° to about 20°, such about as 15°.

One or more regions of the primary and/or secondary bone plates may be configured for contacting and being attached to a bone portion. Hence, in certain embodiments, the primary or secondary bone plate includes one or more openings, such as an opening that spans the thickness of the bone plate and extends between a bottom or bone contacting surface and a top surface thereof. The opening may be of any suitable configuration, and in some embodiments, the opening is adapted to receive a fastener so as to attach the bone plate to a bone portion. Accordingly, in certain embodiments, the primary and/or secondary bone plate includes one or more, e.g., a plurality of openings, wherein the openings are positioned in a distal, intercalating, and/or proximal portion of the primary and/or secondary bone plate.

For instance, one or more of a proximal, intercalating, or distal region and/or engagement element of the primary and/or secondary bone plate may include one or more openings. For example, the distal body portion of the primary bone plate may include an opening that is configured for receiving a fastener, such as a fastener that is adapted so as to attach the primary bone plate to a bone portion, e.g., a first bone portion. In certain variations, an intercalating or a proximal portion of the primary bone plate is configured for being attached to a bone portion and thus may include one or more openings. For instance, the engagement element of the primary or secondary bone plate may include an opening positioned in the proximal portion of the bone plate that is adapted for receiving a fastener, such as a fastener that may be inserted through the opening and functions to couple the primary bone plate to an additional, secondary bone plate, and/or a bone portion, e.g., a second bone portion.

This opening, as well as any other opening included in the bone plate system, may be of any suitable configuration. For instance, the opening may be round, e.g., circular or semi-circular, triangular, square, ovoid, arced, elliptical, or the like. For instance, in certain embodiments, the opening is circular and in certain embodiments the opening is semi-circular, arced, or ovoid. In certain embodiments, two or more openings are included and positioned at the proximal portion of the primary and/or secondary bone plate. For instance, in certain embodiments, one or more openings are circular and an additional one or more openings is semi-circular or arced or ovoid. Where an opening is circular, it may have a diameter that ranges from about 0.5 mm to about 5 mm, such as from about 1 mm to about 4 mm, including about 2 mm or about 2.5 mm to about 3 mm. Where an opening is ovoid, it may have a width that ranges from about 0.5 mm to about 5 mm, such as from about 1 mm to about 4 mm, including about 2 mm or about 2.5 mm to about 3 mm; and it may have a length that ranges from about 2 mm to about 15 mm, such as from about 5 mm to about 9 or about 10 mm, including about 7 mm to about 8 mm.

In certain variations, the distal body portion of the secondary bone plate may include an opening that is configured for receiving a fastener, such as a fastener that is adapted so as to attach the secondary bone plate to a bone portion, e.g., a third bone portion. In certain variations, one or more openings, as described herein, include threading such as threading that corresponds to threading positioned on a fastener. In at least this manner, a fastener may be inserted into and through the opening by rotating the fastener in such a manner that the threads of the fastener align with the corresponding threads of the opening. In certain embodiments, one or more openings do not include threading such that the fastener may be inserted there through without threading the fastener into the opening.

As can be seen above, a subject primary bone plate with reduction aids, and/or bone plate system, may have a variety of configurations adapted to capture fracture fragments, which may be distanced from a primary bone portion, so as to reduce the fragmented portion(s) in correct alignment with another, e.g., primary, bone portion and thereby stabilize the fracture portions and facilitate the appropriate healing of the fractured and/or fragmented bone. To that extent, the bone plate(s) of the present bone plate system may include a multiplicity of elements, for instance, engagement elements, which may include tab and tab receiving portions of varying angles; as well as openings, such as apertures of differing configurations that are adapted to receive and align a fastener at varying orientations to the bone plate and/or underlying bone. In this manner, the bone plates and systems set forth herein provide a flexible interface for reducing and stabilizing fractures, including peri-articular fractures that are out of plane from a main, primary bone shaft.

DESCRIPTION OF THE FIGURES

As summarized above, aspects of the disclosure include a primary bone plate that includes one or more projections, or reduction aids, extending away from a portion, e.g., a side or end portion, thereof. The primary bone plate with reduction aids may be used alone or in conjunction with another, e.g., secondary, bone plate so as to form a system. Due to the adaptability of the primary bone plate, and/or bone plate system, to differing bone morphologies, the primary bone plate and system are well suited for reducing, aligning, and/or fixing commutated fractures, for instance, wherein the fracture includes a fragmented bone portion, such as a fragmented bone portion that is distal to a primary bone shaft portion and/or positioned at an angle thereto. For example, the primary bone plate with reduction aids and/or bone plate system may be configured so as to reduce, align, and/or fix one or more fragmented bone portions, wherein the fragmented bone portions may be distanced and/or out of plane from one another, so as to treat a bone fracture.

Accordingly, the primary bone plate and system may include a single, e.g., a primary bone plate, or a plurality of bone plates, which bone plate(s) may be configured for being attached to one or more bone portions, and in variations where a system is provided, may be adapted to be coupled together with one another so as to reduce, fix and/or stabilize the one or more bone portions in correct anatomical and/or healing alignment for the treatment of a bone fracture. Reference will now be made in detail to various embodiments of the disclosure, which are illustrated in the accompanying figures.

Referring now to FIG. 1, a primary or secondary bone plate of the present disclosure is set forth. FIG. 1A provides a front view of the primary bone plate 10, FIG. 1B provides a perspective view of a slightly modified bone plate of FIG. 1A, and FIG. 1C provides a side view of the bone plate of FIG. 1B. The primary bone plate 10 includes an extended, elongated body 20. The elongated body 20 is substantially planar, and includes a distal portion 22 with a distal end 23, a proximal portion 25 with a proximal end 26, and an intercalating portion 24 between the distal and proximal portions.

The primary bone plate 10 additionally includes a first side 27 and a second side 28 as well as a bone contacting surface 21 and a top surface 29. The distal portion 22, specifically, the distal end 23, includes a plurality of projections, or reduction aids, 40a and 40b.

The reduction aids, 40a and 40b, include an extended, elongated body 41a and 41b. The elongated bodies 41a and 41b include a proximal portion 42a and 42b with a proximal end 43a and 43b, a distal portion 45a and 45b with a distal end 46a and 46b, and an intercalating portion 44a and 44b between the distal and proximal portions.

The elongated body 20 of the primary bone plate 10 additionally includes a plurality of openings, 15a and 15b, positioned in the proximal portion 25 of the elongated body 20. The elongated body 20 additionally includes a plurality of openings, 15d and 15e, positioned in the distal portion 22 of the elongated body 20. The elongated body 20 also includes an opening, 15c, positioned in the intercalating portion 24 of the elongated body. The openings extend between the bone contacting surface 21 and the top surface 29 of the elongated body. As depicted, openings 15a, 15b, and 15d are recessed, round or circular, opening 15c is longitudinal and oval, and opening 15e is transverse and oval. It is to be understood that although five openings are illustrated with reference to the various figures, fewer or more openings than illustrated may be included, such as 2, 3, 4, 5, 6, 7, 10, or more openings may be provided. Additionally, the top surface 29 of the primary bone plate 10 substantially corresponds to a primary plane 1.

FIG. 1A depicts a primary bone plate 10 that includes a forked like configuration, wherein the reduction aids 40a and 40b are curved and extend longitudinally away from the distal end 23 of the elongated body 20. The reduction aids 40a and 40b may be configured so as to be inserted within an opening within a bone portion, such as a fragmented and/or displaced bone portion in need of reduction. See for instance, FIG. 2.

Figure 1B:
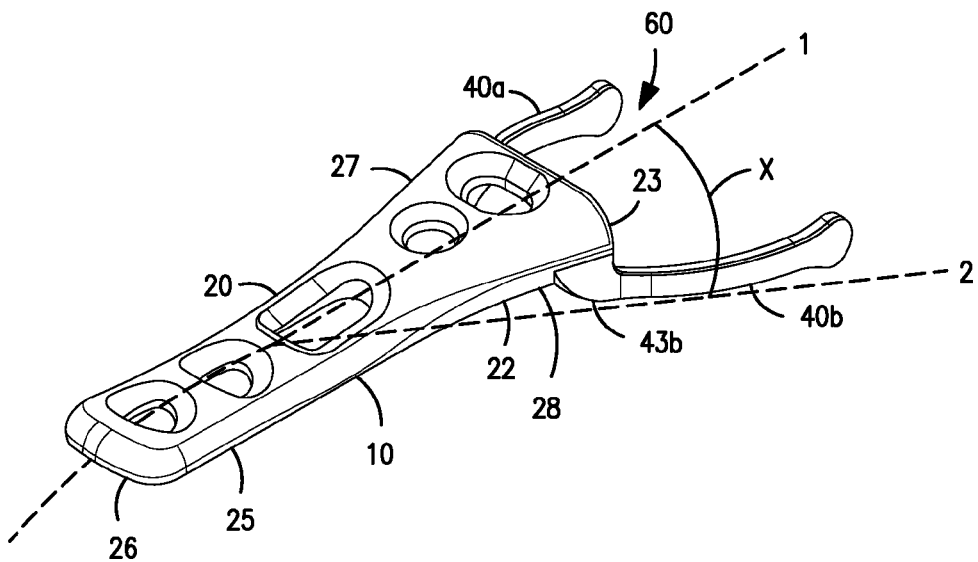
Figure 1C:
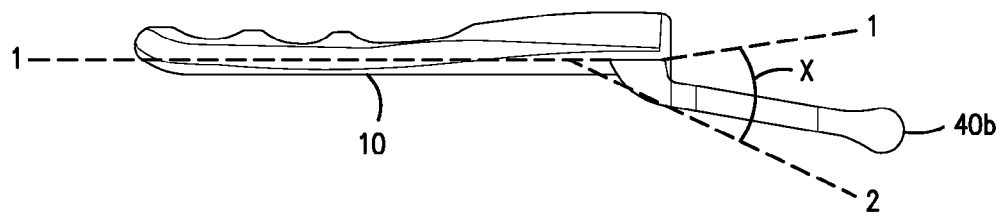

FIGS. 1B and 1C depict a primary bone plate 10 that includes a Y like configuration, wherein each of the reduction aids 40a and 40b are curved and extend axially away from the distal portion 22 of the elongated body 20. Reduction aid 40a extends away from side 27, and reduction aid 40b extends away from side 28. As can be seen with reference to FIG. 1C, the reduction aids 40a (not shown) and 40b extend axially away from sides 27 (not shown) and 28, respectively, at an angle X, defined by axis 1 and axis 2. The reduction aids 40a and 40b may be configured so as to be inserted within an opening within a bone portion, such as a fragmented and/or displaced bone portion in need of reduction (see for instance, FIG. 3), or the reduction aids 40a and 40b may be configured so as to include an opening 60 there between within which opening 60 a bone portion may be inserted (See for instance, FIG. 6).

Figure 1D:
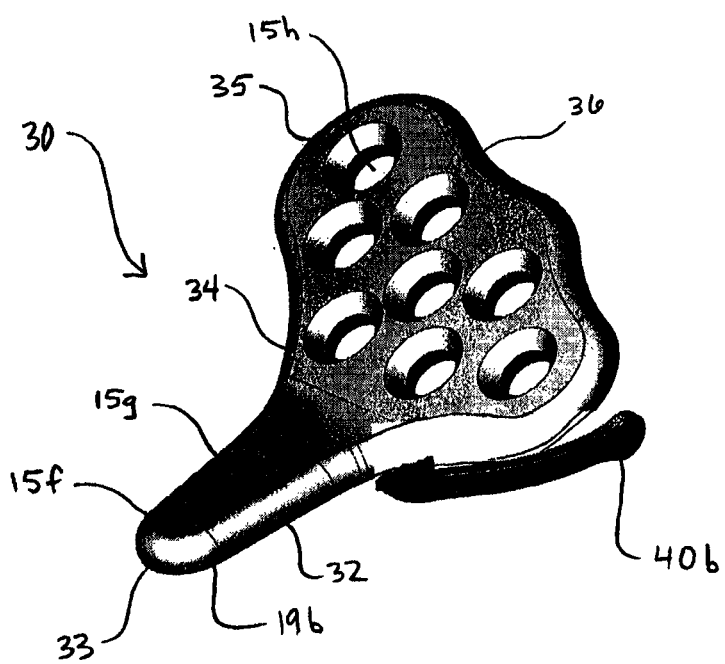
Figure 1E:
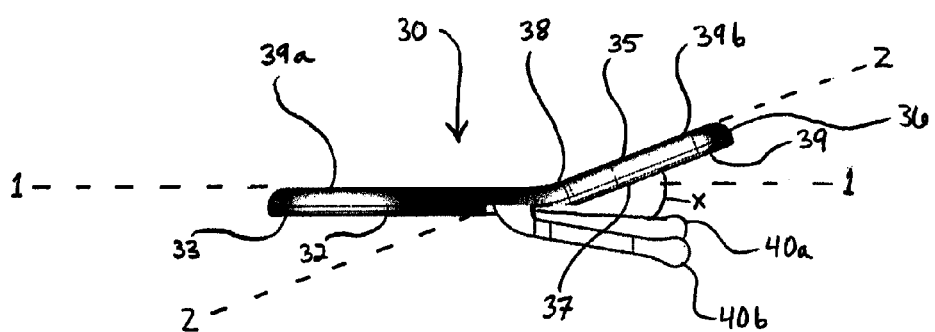

FIG. 1D provides a top, perspective view of a secondary bone plate 30, FIG. 1E provides a side view of the bone plate of FIG. 1E. The secondary bone plate 30 includes an extended body that in turn includes a proximal portion 32 with a proximal end 33, a distal portion 35 with a distal end 36, and an intercalating portion 34 between the distal and proximal portions. As depicted the distal portion 35 is angled with respect to the proximal portion 32. Specifically, a plane 1 defined by the top surface 39a of the proximal portion 32 transects plane 2 defined by the top surface 39b of the distal portion 35. See for instance, FIG. 1E. As illustrated the secondary bone plate 30 includes a plurality of reduction aids 40a and 40b which are curved and extend axially away from the proximal/intercalating portions 32 and 34 of the extended body of the secondary plate 30. Reduction aid 40a extends away from side 37, and reduction aid 40b extends away from side 38. As can be seen with reference to FIG. 1E, the reduction aids 40a and 40b extend axially away from sides 27 and 28, respectively, at an angle X, defined by plane 1.

Figure 2:
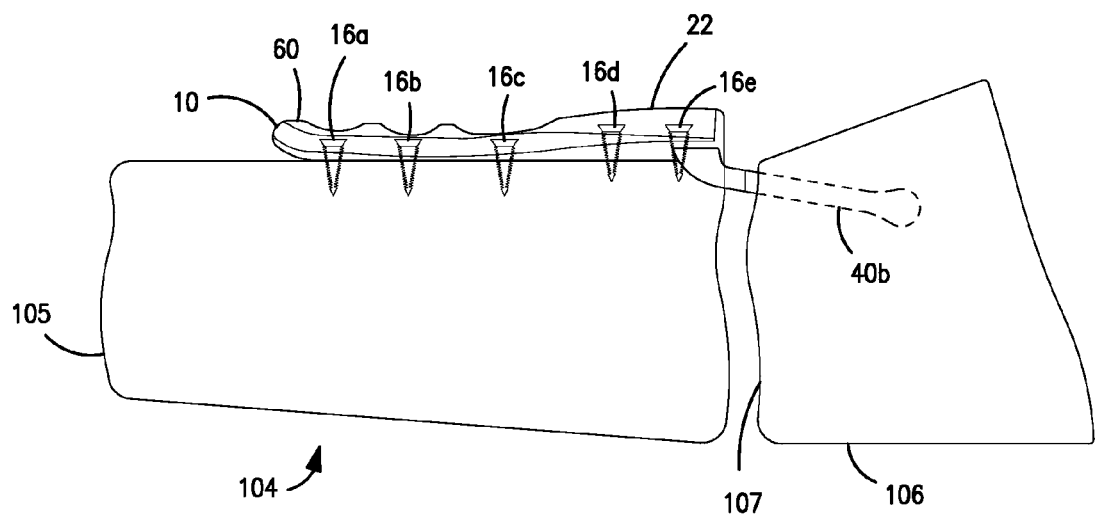
FIG. 2 provides the primary bone plate of FIG. 1A as the bone plate would be used when positioned and attached to a bone portion so as to reduce a fractured and displaced distal fragment.

Referring now to FIG. 2, the primary bone plate 10 of FIG. 1A is set forth as the bone plate 10 would be used when positioned and attached to a non-fractured bone portion 105 of long bone 104, so as to reduce a fractured and displaced distal bone portion 106. As depicted in FIG. 2, the proximal and distal portions 25 and 22 of the primary bone plate 10 are attached to the non-fractured bone portion 105 by insertion of fasteners 16a-e into openings 15a-e of bone plate 10. The reduction aids 40a and 40b of primary bone plate 10 have been inserted into an opening 107 within fractured bone portion 106, such as an opening caused by the fracture of long bone 104 and the displacement of fractured bone portion 106 relative to non-fractured bone portion 105. The reduction aids 40a and 40b may be, but need not be, outwardly biased such that once inserted into the opening 107, the reduction aids 40a and 40b move away from one another so as to contact an inner surface of bone portion 106 and exert an outward force thereon. In at least this manner, the primary bone plate 10 may be associated with fractured bone portion 106 and used to reduce, align, and fix fractured portion 106 in anatomical and/or healing alignment with non-fractured bone portion 105 for the reduction of the fracture there between and the treatment and healing of long bone 104.

Figure 3A:
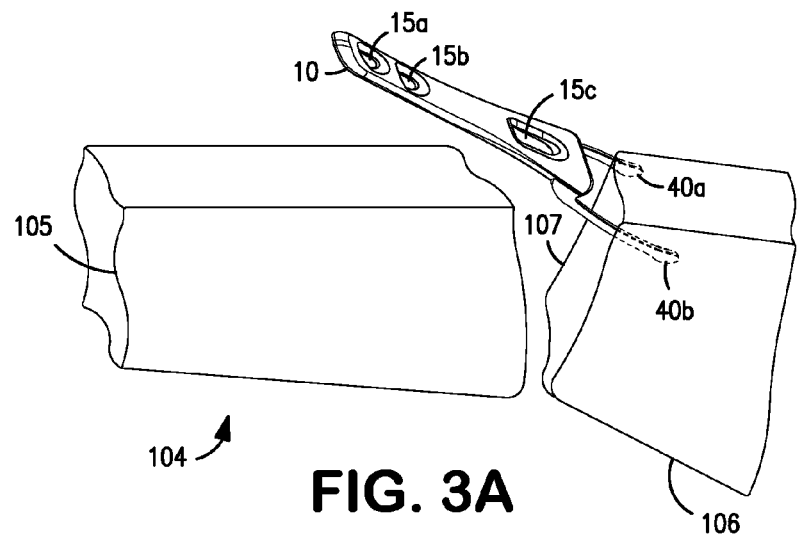
FIGS. 3A-3C provide the primary bone plate of FIG. 1B as the bone plate would be used to reduce a fractured and displaced bone portion.
Figure 3B:
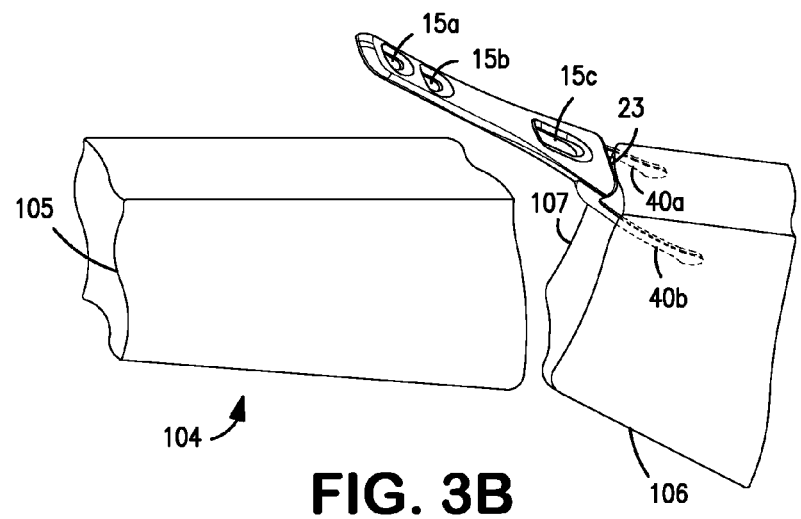
Figure 3C:
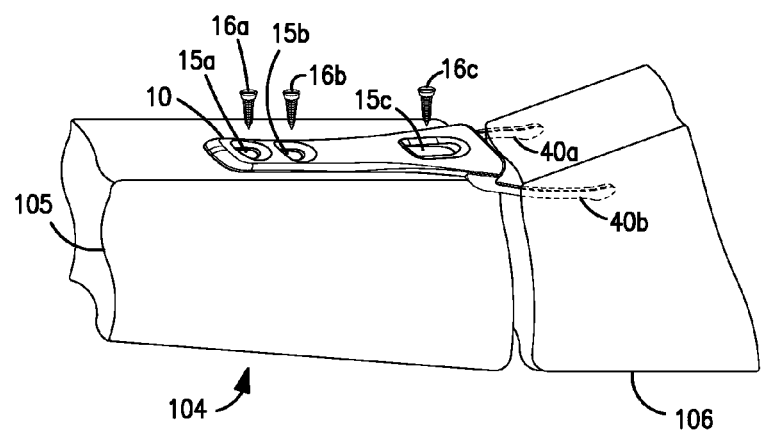

Referring now to FIG. 3, the primary bone plate 10 of FIG. 1B is set forth as the bone plate 10 would be used to reduce a fractured and displaced bone portion 106 of long bone 104. As can be seen with reference to FIG. 3A the reduction aids 40a and 40b of primary bone plate 10 are inserted into an opening 107 in fractured bone portion 106 of long bone 104. As can be seen with reference to FIG. 3B the reduction aids 40a and 40b may be inserted into the opening 106 in such a manner that the distal end 23 of the bone plate 10 abuts the fractured bone portion 10. Once inserted, the reduction aids 40a and 40b can be used to reduce and align the fractured bone portion 106 in correct anatomical and/or healing alignment with non-fractured bone portion 105. When the two bone portions are aligned, fasteners 16a-c may be inserted into openings 15a-c so as to fasten bone plate 10 onto bone portion 105, so as to treat and heal the fracture in bone 104.

Figure 4:
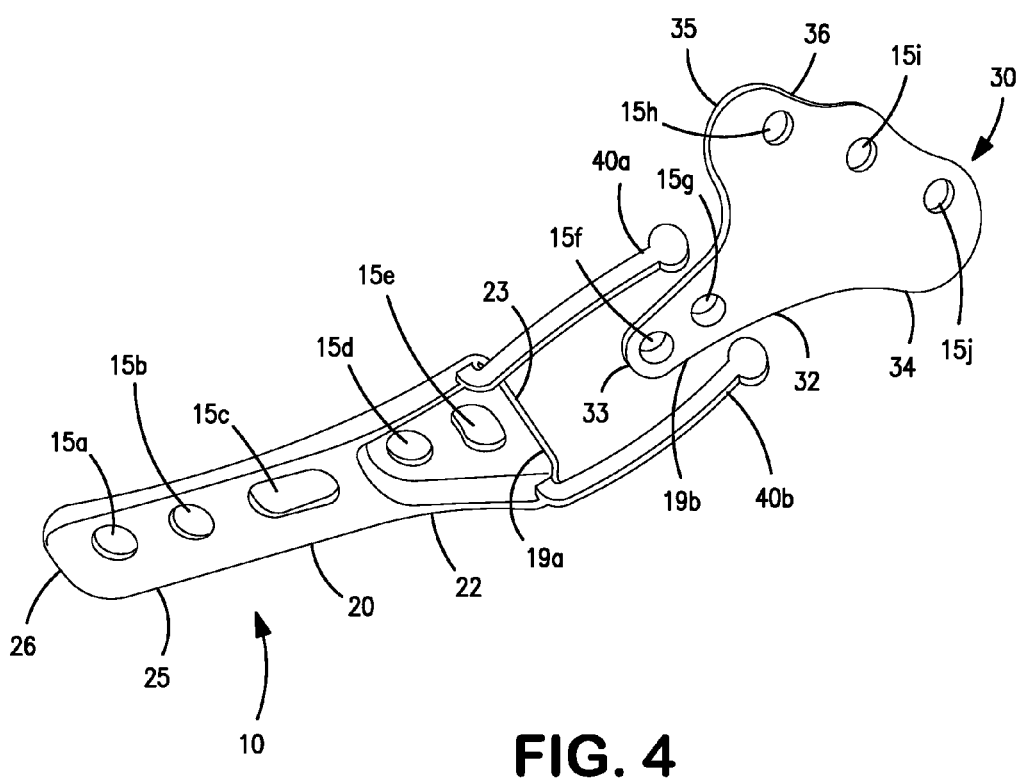
FIG. 4 provides a bone plate system of the disclosure, which bone plate system includes a plurality of bone plates, for instance, a first or primary bone plate with reduction aids, and a secondary bone plate.

As described above, an aspect of the disclosure provides for a bone plate system. The bone plate system may be employed to reduce and/or fix one or more bone portions for the treatment of a bone fracture, for example. As illustrated in FIG. 4, the bone plate system includes a plurality of bone plates, for instance, a first or primary bone plate with reduction aids, which bone plate may be a diaphyseal bone plate, and a second or secondary bone plate, which bone plate may be a juxtaarticular bone plate. The primary bone plate with reduction aids and the secondary bone plate may be configured for being attached to one or more bone portions and may be adapted to be coupled together with one another so as to reduce, fix and/or stabilize, for example, the one or more bone portions in healing alignment for the treatment of a bone fracture.

As illustrated in FIG. 4, a bone plate system 5 is provided. The system 5 includes a primary bone plate 10 and a secondary bone plate 30. The primary bone plate 10 includes an elongated body 20 that includes a proximal portion 25 with a proximal end 26, a distal portion 22 with a distal end 23, and an intercalating portion 24 positioned between the proximal portion 25 and distal portion 22. The proximal portion 25 includes openings 15a and 15b, the intercalating portion 24 includes opening 15c, and distal portion 22 includes openings 15d and 15e, which openings are recessed and configured for receiving a fastener there through. The distal portion 22 includes reduction aids 40a and 40b, as well as secondary bone plate engagement element 19a, which engagement element 19a is configured as a raised, hooded slot into which a bone plate engagement element 19b of secondary bone plate 30 may be received. The raised, hooded slot is tapered. Specifically, the raised, hooded slot is wider adjacent the distal end 23 of the elongated body 20 of the primary bone plate 10 and becomes narrower with increasing distance from the distal end 23 toward the proximal end 26.

The secondary bone plate 30 includes an extended body that includes a distal portion 35 with a distal end 36, a proximal portion 32 with a proximal end 33, and an intercalating portion 34 positioned between the distal portion 35 and proximal portion 32. The distal portion 35 includes openings 15h, 15i, and 15j; and the proximal portion 32 includes openings 15f and 15g, which openings are recessed and configured for receiving a fastener there through. The proximal portion 32 includes a primary bone plate engagement element 19b, which engagement element 19b is configured as a tab insertion portion that is configured so as to be fitted and received within the raised, hooded bone plate engagement element 19a of primary bone plate 10. The insertion tab portion is tapered. Specifically, the insertion tab portion is narrower adjacent the proximal end 33 of the extended body of the secondary bone plate 30 and becomes wider with increasing distance from the proximal end 33 toward the distal end 36.

As depicted, the primary and secondary bone plates are substantially planar relative to a top or bottom surface thereof. However, in certain embodiments, the primary and secondary bone plates are configured such that at least a top and/or bottom surface of one of the bone plates is at an angle with respect to the top and/or bottom surface of the other bone plate. For instance, one or more surfaces of the bone plates may include an arc, curvature or angle such that a plane of the surface one bone plate is angled with respect to a plane of a surface on the other bone plate. Such an embodiment is provided with respect to the bone plate system illustrated in FIG. 5.

As can be seen with respect to FIG. 5, a bone plate system 5 is provided. The bone plate system 5 includes a primary bone plate 10 and a secondary bone plate 30. The primary bone plate 10 includes a proximal portion 25, an intercalating portion 24, and a distal portion 22. The proximal portion 25 includes openings 15a and 15b. The distal portion 22 includes reduction aids 40a and 40b (not shown), as well as a bone plate engagement portion 19a. The bone plate engagement element 19a is configured as a raised, hooded slot into which a bone plate engagement element 19b of secondary bone plate 30 may be received.

The secondary bone plate 30 includes an extended body that includes a distal portion 35, an intercalating portion 34, and a proximal portion 32. The distal portion 35 includes openings 15h, 15i, and 15j; and the proximal portion 32 includes openings 15f and 15g. The proximal portion 32 includes a primary bone plate engagement element 19b. The primary bone plate engagement element 19b is configured as a tab insertion portion that is configured so as to be fitted and received within the raised, hooded secondary bone plate engagement element 19a of primary bone plate 10.

As illustrated, the primary and secondary bone plates 20 and 30 are configured such that when coupled to one another, one or more surfaces thereof are at an angle to each other. For instance, as depicted, long bone 104 includes a first bone portion 105 and a second bone portion 106, wherein the two bone portions are out of plane from one another. Specifically, the first bone portion 105 includes a surface that corresponds to a first plane, e.g., a primary plane 1. The second bone portion includes a surface that corresponds to a second plane, e.g., a secondary plane 2. As can be seen with reference to FIG. 5, the primary 1 and secondary 2 planes are anti-parallel to one another.

Accordingly, due to the curved and/or angled morphology of the fractured bone 104, the primary 20 and secondary 30 bone plates are adapted such that their configuration conforms to the morphology of the bone portions 105 and 106, respectively, to which the bone plates are to be attached. Specifically, in the variation illustrated in FIG. 5, the primary bone plate engagement element 19b of the secondary bone plate 30 is configured such that it recapitulates a desired angle, such as the angle of the non-planar bone portion 106. As described above, the angle of the bone plate engagement element may be configured such that it allows the primary and/or secondary bone plate to conform to any suitable bone morphology to which the bone plate is to be attached, such as the angle of a volar radius. Thus, as illustrated in FIG. 5B, the coupling of the secondary bone plate angled tab insertion portion 19b into the hooded tab receiving portion 19a of the primary bone plate 20 produces a natural reduction of the radius platform.

Figure 5A:
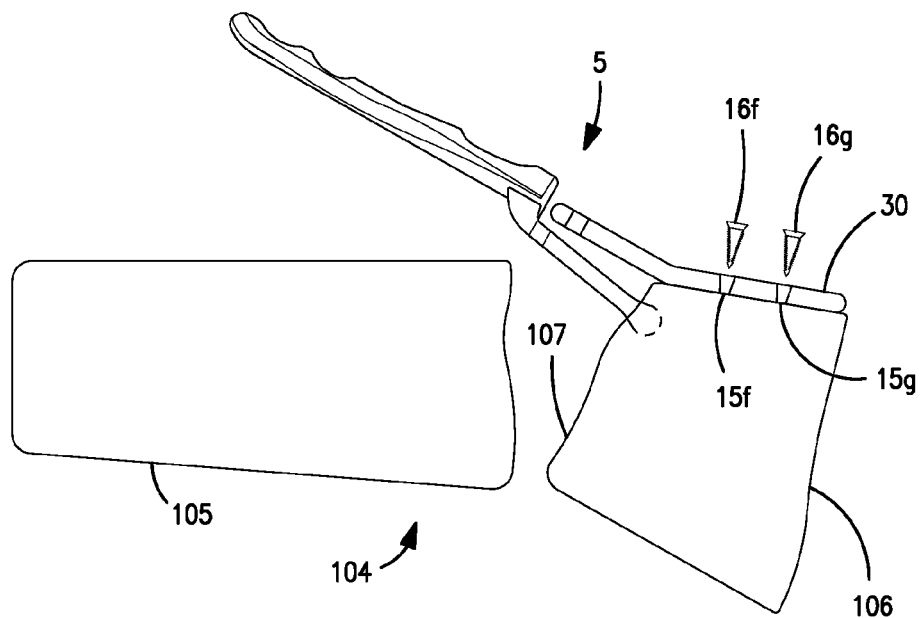
FIGS. 5A and 5B provide the bone plate system of FIG. 1B as the bone plate system would be used when positioned and attached to a bone portion so as to reduce a fractured and displaced distal fragment.
Figure 5B:
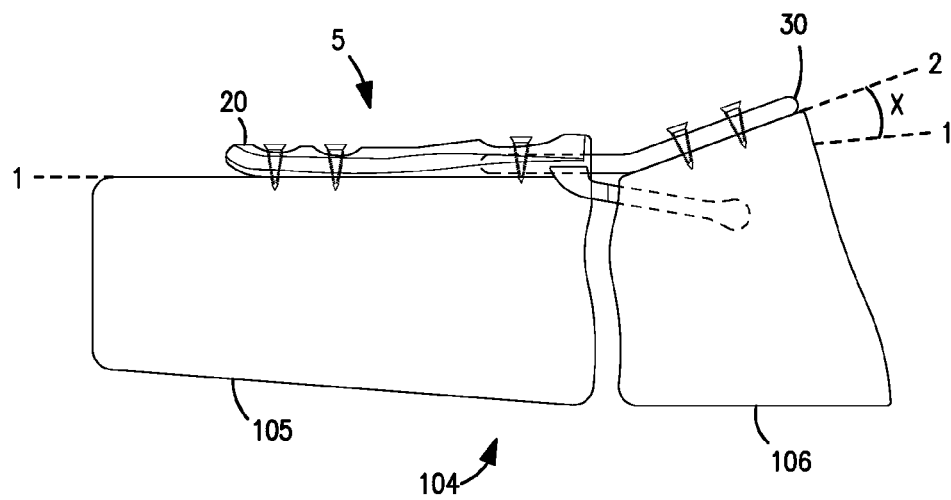

Specifically, as can be seen with respect to FIG. 5A, the secondary bone plate 30 may be associated with a fractured bone portion 106. The fractured bone portion 106 may be any fractured bone portion, for instance, in certain embodiments, the fractured bone portion is a peri-articular bone portion, such as a fractured metaphyseal or epiphyseal bone portion, and the secondary bone plate 30 is positioned along a plane (e.g., a secondary plane) pertaining thereto. The secondary bone plate 30 may be attached to the fractured peri-articular bone portion 106 via the insertion of fasteners 16f and 16g into openings 15f and 15g in distal portion 32 of secondary bone plate 20.

The reduction aids 40a and 40b of primary bone plate 10 may be inserted into the opening 107 in fractured bone portion 106 of long bone 104. Once inserted, the reduction aids 40a and 40b can be used to reduce and align the fractured peri-articular bone portion 106 in correct anatomical and/or healing alignment with non-fractured bone portion 105, which fractured bone portion may be a diaphyseal bone portion. When the two bone portions 106 and 105 are aligned, the angled tab insertion portion 19b of the secondary bone plate 30 may be inserted into the hooded tab receiving portion 19a of the primary bone plate 20. The primary bone plate 20 may be associated with the bone portion 105, e.g., diaphyseal bone portion, positioned along a plane 1, e.g., a primary plane, pertaining thereto, and attached to the bone portion 105 by insertion of fasteners 16a-c into openings 15a-c so as to fasten bone plate 10 onto bone portion 105.

In such an instance, the configuration(s) of the primary, e.g., diaphyseal, and secondary, e.g., peri-articular, plates 20 and 30, respectively, as well as the engagement elements 19a and 19b there between, are such that the two bone plates are coupled with one another so as to correctly reduce, align, stabilize, and/or restore the two bone portions 105 and 106 to a position that at least approximates their natural position and thereby treats the bone fracture in long bone 104. Accordingly, given the adaptable configurations of the various elements of the bone plate system disclosed herein, the present system is capable of reducing and fixing a bone fracture, such as a fracture of the radius bone, wherein a portion of the fragmented bone resides in a position that is distal to a fracture in a primary bone portion.

Figure 6A:
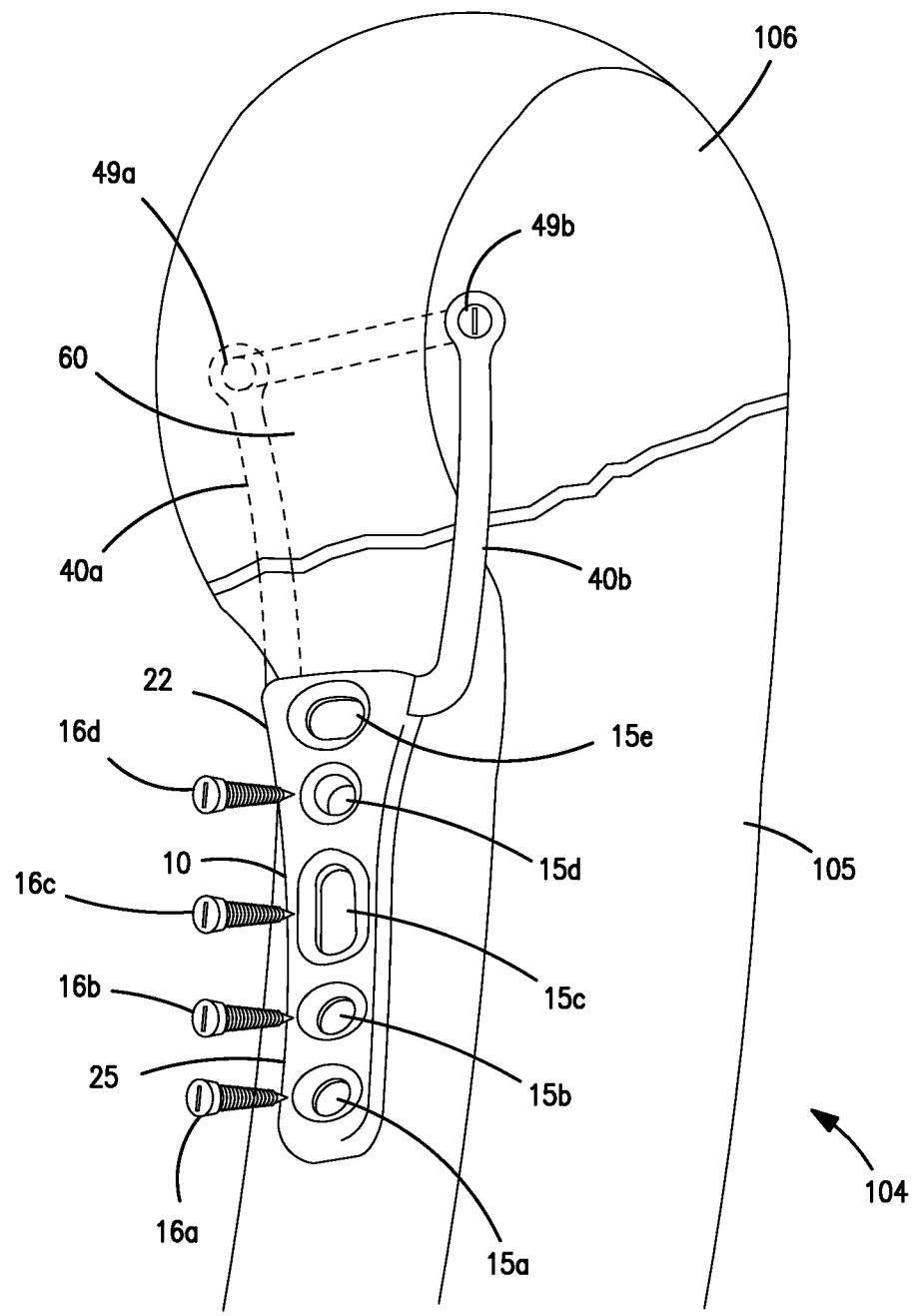
FIG. 6A provides a primary bone plate of the disclosure including reduction aids in a Y-like configuration such that the tines of the reduction aids are configured for engaging opposed extramedullary bone surfaces.

As can be seen with reference to FIG. 6, a primary bone plate 10 of the disclosure including reduction aids 40a and 40b extending from a distal portion 22 thereof may have a Y like configuration, wherein each of the reduction aids 40a and 40b are curved and extend axially away from the distal portion 22 of the elongated body 20. As depicted, the reduction aids 40a and 40b are configured so as to include an opening 60 there between within which opening 60 a bone portion 106 is inserted. FIG. 6A depicts the primary bone plate 10 as it would be used when positioned and attached to both a non-fractured bone portion 105 and fractured bone portion 106 of long bone 104, so as to align, reduce and stabilize the fractured bone portion 106 with respect to the non-fractured bone portion 105.

Figure 6B:
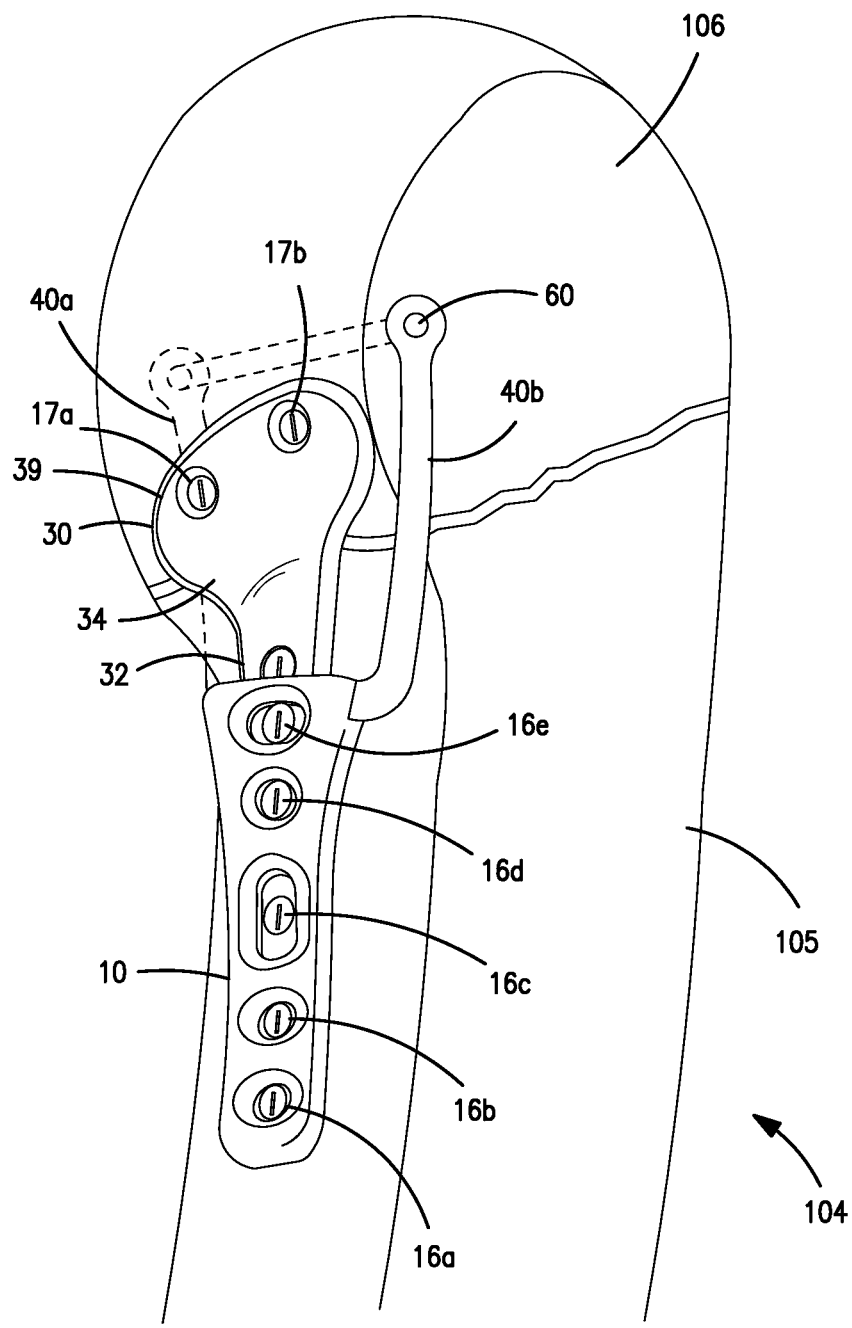
FIG. 6B provides a primary bone plate system of the disclosure including a primary bone plate with reduction aids in a Y-like configuration such that the tines of the reduction aids are configured for engaging opposed extramedullary bone surfaces, and a secondary bone plate configured for being coupled with the primary bone plate.

As illustrated in FIGS. 6A and 6B, the proximal and distal portions 25 and 22 of the primary bone plate 10 are attached to the non-fractured bone portion 105 by insertion of fasteners 16a-d into openings 15a-d of bone plate 10. The reduction aids 40a and 40b of primary bone plate 10 have been positioned so that each reduction aid 40a and 40b straddles an opposing surface of bone portion 106. The bone plate is positioned such that the reduction aids 40a and 40b span the fracture site. As depicted, reduction aids 40a and 40b include openings 49a and 49b therein through which fastener 60 has been inserted. Additionally, the reduction aids 40a and 40b may be, but need not be, inwardly biased such that once positioned so as to straddle bone portion 106, the reduction aids 40a and 40b move toward one another so as to contact opposed outer surfaces of bone portion 106 and exert an inward force thereon. In at least this manner, the primary bone plate 10 may be associated with fractured bone portion 106 and non-fractured bone portion 105 and used to reduce, align, and fix fractured portion 106 in anatomical and/or healing alignment with non-fractured bone portion 105 for the reduction of the fracture there between and the treatment and healing of long bone 104.

As illustrated in FIG. 6B, a bone plate system 5 in accordance with the disclosure is provided. FIG. 6B depicts the bone plate system 5 as it would be used when positioned and attached to so as to align, reduce and stabilize a fractured bone portion 106 with respect to a non-fractured bone portion 105 of long bone 104. The bone plate system 5 includes a primary bone plate 10 with reduction aids 40a and 40b, aligned and positioned as described above with respect to FIG. 6A. The primary bone plate 10 of FIG. 6B, however, includes a bone plate engagement element 19a, which element is configured for being associated with a bone plate engagement element of a secondary bone plate. Specifically, the distal portion 22 of primary bone plate 10 includes reduction aids 40a and 40b, as well as a bone plate engagement element 19a, which engagement element 19a is configured as a raised, hooded slot into which a bone plate engagement element 19b of secondary bone plate 30 may be received.

The system, therefore, of FIG. 6B includes a secondary bone plate 30. The secondary bone plate 30 includes an extended body that includes a distal portion 35, a proximal portion 32, and an intercalating portion. The distal portion 35 and proximal portion 32 includes a plurality of openings. The proximal portion 32 includes a primary bone plate engagement element 19b, which engagement element 19b is configured as a tab insertion portion that is configured so as to be fitted and received within the raised, hooded secondary bone plate engagement element 19a of primary bone plate 10. The intercalating portion 34 includes a bend, such that the distal portion 35 is angled and/or curved with respect to the proximal portion 32. Accordingly, as depicted, the primary and secondary bone plates are angled relative to a top or bottom surface thereof. Specifically, a top surface of the secondary bone plate is out of plane with a plane 1 defined by the top surface of the primary bone plate.

As depicted in FIG. 6B, the secondary bone plate may be positioned on bone portion 106 so that the bone plate engagement element 19b of the secondary bone plate 30 spans the line of demarcation for the fracture. The secondary bone plate 30 may then be attached to the bone portion 106, for instance, via fasteners 17a and 17b inserted through openings extending through the extended body of the distal portion 35 of the secondary bone plate 30.

The primary bone plate 10 is positioned with respect to the secondary bone plate 30, such that the bone plate engagement element 19a of the primary plate 10 aligns with the bone plate engagement element 19b of the secondary plate 30, and the reduction aids 40a and 40b straddle bone portion 106. Fastener 60 may then be inserted through openings in the reduction aids 40a and 40b, and pursuant to that association, the primary bone plate 10 may be used to properly align bone portion 106 with bone portion 105, for instance, like a joy stick, and once the appropriate alignment has been obtained, the primary and secondary bone plates may be coupled together, for instance, by the joining of their respective bone plate engagement elements 19a and 19b. The primary and secondary bone plates may then be attached to one another, for instance, by insertion of fasteners 16d and 16e through openings in the respective bone plates. In at least this manner, the primary bone plate 10 may be associated with fractured bone portion 106 and non-fractured bone portion 105 and used to reduce, align, and fix fractured portion 106 in anatomical and/or healing alignment with non-fractured bone portion 105 for the reduction of the fracture there between and the treatment and healing of long bone 104.

Methods of Use

In one aspect, the subject matter described herein is directed to methods of using such bone plate systems, as described herein above, so as to align, reduce and/or fix one or more fractured bone portions for the treatment thereof, for example. Accordingly, in certain embodiments, a general method is provided for reducing a bone fracture, wherein the method includes the steps of providing at least a first bone plate. The first bone plate may itself by configured for aligning and reducing a bone fracture on its own, or the first bone plate may be configured for being used in conjunction with a second bone plate, wherein the first and second bone plates are configured for being coupled to one another. As noted above, the first and/or second bone plates may include portions that are angled or curved with respect to one another and at least one of the first or second bone plates includes at least one reduction aid, e.g., a plurality of reduction aids, associated therewith.

Generally the method includes positioning the reductions aids located at a distal portion of the bone plate within or around a fractured bone portion so that the reduction aids either enter into an intramedullary portion of the bone or contact opposed extramedullary surfaces thereof. In this manner, the fractured bone portion may be contacted by the plurality of reduction aids. Once the reduction aids are properly positioned in relation to the bone portion, the proximal portion of the bone plate may be used, for instance like a joystick, to align the fractured bone portion in correct anatomical alignment with a non-fractured bone. Once the two bone portions have been properly aligned the bone plate may be attached to the surface of the respective bone portion(s) by the insertion of fasteners, or the like, there through so as to reduce and stabilize the bone fracture or it may be coupled, dependent on its configuration and intended use, to another bone plate.

For example, where a bone plate system is provided, the bone plate system may include a first or primary bone plate and a second or secondary bone plate where the primary bone plate includes a plurality of reduction aids. The reduction aids of the primary bone plate may be associated with a bone fragment, as described above, and the primary bone plate may be attached to a bone portion, for instance, a first bone portion that is positioned proximal to a locus of a fracture. The reduction aids of the primary bone plate may be inserted into an intramedullary bone portion of a second bone portion or may be positioned such that they contact opposed extramedullary surfaces thereof, as described above. The second bone plate may be attached the second bone portion. The bone plates may be attached to their respective bone portions in any suitable order. For instance, the primary bone plate may be attached to a first bone portion prior to the attachment of the secondary bone plate to a second bone portion or vice-versa. However, regardless of the order of the attachment of the primary and secondary plates, the tines of the primary bone plate may be used as a lever so as to obtain correct anatomical alignment of the bone portions and the primary bone plate may then be attached to the proximal bone portion.

The application of a first or secondary bone plate to a bone portion may, but need not, involve the use of a K-wire. For instance, the application of the secondary bone plate to a distal fragmented bone portion may involve the use of K-wire, wherein K-wire may be inserted through an opening in the secondary bone plate, for instance, in the distal portion thereof, so as to be used as a guide to insure correct alignment of the secondary bone plate to the distal fractured bone portion. Accordingly, the K-wire to be applied may be drilled parallel to an articular surface, such as in the lateral plane of the bone fragment. The secondary plate may then be slid over the K-wire and down to the surface of the distal bone fragment. Once contacted and correctly positioned with respect to the distal bone fragment the secondary bone plate may be attached thereto by the insertion of one or more fasteners, e.g., pegs, through openings in the secondary bone plate. K-wire may also be used to perform this function in addition or substitution for the referenced pegs.

If the primary plate has not heretofore been attached to the primary bone portion it may then be attached to its respective bone portion, for instance, in the manner described above. It is to be noted that the primary and/or secondary bone plate (if included) are not only specifically designed, as described above, to conform to the morphology of the bone portions to which they are attached, but are also designed such that when the primary and secondary bone plates are attached to their respective bone portions, the coupling of the primary and secondary bone plates to one another results in the alignment and proper reduction of the respective bone portions such that when the primary and secondary bone plates are attached to one another the fractured bone portions are stabilized in an alignment that approximates the normal anatomical alignment that the bone was in prior to the fracture and therefore promotes correct and rapid healing, with minimal adverse effects.

As certain changes may be made without departing from the scope of the present subject matter described herein, it is intended that all matter contained in the above description or shown in the accompanying drawings be interpreted as illustrative and not in a literal sense (and thus, not limiting). Practitioners of the art will realize that the method, device and system configurations depicted and described herein are examples of multiple possible system configurations that fall within the scope of the current subject matter described herein.

While the subject matter described herein has been described with reference to the specific embodiments thereof, it should be understood by those skilled in the art that various changes may be made and equivalents may be substituted without departing from the true spirit and scope of the subject matter described herein. In addition, many modifications may be made to adapt a particular situation, material, composition of matter, process, process step or steps, to the objective and scope of the subject matter described herein. All such modifications are intended to be within the scope of the claims appended hereto.

Throughout this application, various publications, patents and published patent applications may be cited. The disclosures of these publications, patents and published patent applications referenced in this application are hereby incorporated by reference in their entirety into the present disclosure. Citation herein by the Applicant of a publication, published patent application, or patent is not an admission by the Applicant of said publication, published patent application, or patent as prior art. Accordingly, all publications and patents cited in this specification are herein incorporated by reference as if each individual publication or patent were specifically and individually indicated to be incorporated by reference.

What is claimed is:

1. A bone plate system comprising:
    (a) a primary bone plate;
    (b) a secondary bone plate; and
    (c) a fastener to connect the primary bone plate to the secondary bone plate,
    the primary bone plate comprising:
        (i) an elongated body comprising
            a first and a second side,
            a distal portion having a distal end,
            a proximal portion having a proximal end,
            a surface extending between the first and second sides and the distal and proximal portions,
            a first bone plate engagement element capable of engaging the secondary bone plate so as to allow the primary and secondary bone plates to be coupled to one another, and
            a plurality of openings including a first bone plate connection opening in the first bone plate engagement element, the first bone plate connection opening having a shape with a longer dimension oriented transverse to a length of the elongated body, the length extending along a longitudinal axis of the elongated body; and
        (ii) two bone contacting arms contiguous with the elongated body and projecting away from each side of one of the distal and proximal portions of the elongated body, said one of the distal and proximal portions having a greater width measured between the first and second sides than the other of the distal and proximal portions,
        the surface comprising a bone contacting surface and top surface,
        each arm having a length and being free of any opening, each arm also including a first portion adjacent the elongated body and a second portion spaced along the length of the arm from the first portion and from the elongated body, the first portion of each arm comprising a majority of the length of each arm, each arm further including a side surface extending along the length of the arm in both the first and second portions of the arm, the side surface of the arm having a length extending along the length of the arm and a width extending perpendicular to the length of the arm, the side surface of the second portion of each arm being flat and having its width enlarged relative to the width of the side surface of the first portion of the arm, the enlarged flat side surface of the second portion of each arm facing the enlarged flat side surface of the second portion of the other arm, the second portion of each arm including the enlarged flat side surface of the second portion being an intramedullary bone contacting portion and including an intramedullary bone contacting end, the arms aiding in the reduction of a fractured bone portion, at least one of the bone contacting surface and the top surface defining a primary plane, the arms being disposed on a common side of the primary plane and projecting away from the primary plane at an angle to the primary plane, both the first portion and the second portion of each arm projecting away from said one of the distal and proximal portions of the elongated body in a direction lengthwise of the elongated body, the first bone plate engagement element being located between the two bone contacting arms on said one of the distal and proximal portions of the elongated body having a greater width measured between the first and second sides than the other of the distal and proximal portions, the secondary bone plate comprising an extended body that comprises
- a first and a second side,
- a distal portion having a distal end,
- a proximal portion having a proximal end,
- a surface extending between the first and second sides and the distal and proximal portions,
- a second bone plate engagement element capable of engaging the first bone plate engagement element so as to allow the primary and secondary bone plates to be coupled to one another, and
- a plurality of openings including a second bone plate connection opening in the second bone plate engagement element, one of the first and second bone plate engagement elements including a raised slot configured and dimensioned to receive a tab insertion portion of the other of the first and second bone plate engagement elements such that the first and second connection openings are aligned with each other and such that the secondary bone plate projects away from said one of the distal and proximal portions of the elongated body in said direction in which the arms project away from said one of the distal and proximal portions of the elongated body, the raised slot being tapered to allow the tab insertion portion and the secondary bone plate to be received in a plurality of angular positions relative to the elongated body of the primary bone plate, the fastener being configured and dimensioned to extend through both the first bone plate connection opening and the second bone plate connection opening and into an adjacent bone portion when the first and second connection openings are aligned with each other to connect the primary bone plate to the secondary bone plate and to the adjacent bone portion.

2. The bone plate system according to claim 1, wherein the elongated body further comprises an intercalating portion disposed between the proximal and distal portions.

3. The bone plate system according to claim 2, wherein the openings of the elongated body are positioned in at least one of the distal portion, intercalating portion, and proximal portion.

4. The bone plate system according to claim 1, wherein the arms are separated by a distance, which distance defines an opening between the arms.

5. The bone plate system according to claim 4, wherein the opening between the arms is concave.

6. The bone plate system according to claim 4, wherein the opening between the arms is configured for straddling a bone portion.

7. The bone plate system according to claim 1, wherein each of the arms has a curved portion.

8. The bone plate system according to claim 1, wherein each of the arms is substantially non-curved.

9. The bone plate system according to claim 1, wherein the arms are inwardly biased towards one another.

10. The bone plate system according to claim 1, wherein the arms are outwardly biased away from one another.

11. The bone plate system according to claim 1, wherein each of the arms comprises an extended body that is non-tubular and flat.

12. The bone plate system according to claim 1, wherein the top surface of the distal portion of the elongated body defines the primary plane and the top surface of the proximal portion of the elongated body is out of plane with the primary plane.

13. The bone plate system according to claim 1, wherein the angle at which the arms project away from the primary plane is about 10° to about 30°.

14. The bone plate system according to claim 13, wherein the angle at which the arms project away from the primary plane is about 15° to about 20°.

* * * * *